United States Patent
Risher-Kelly et al.

(10) Patent No.: US 10,390,777 B2
(45) Date of Patent: *Aug. 27, 2019

(54) TRANSFORMABLE IMAGING SYSTEM

(71) Applicant: Medtronic Navigation, Inc., Louisville, CO (US)

(72) Inventors: Clifford M. Risher-Kelly, Wells, ME (US); Ziad F. Elghazzawi, Newton, MA (US); David A. Garlow, Lynnfield, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,272

(22) Filed: Jul. 23, 2018

(65) Prior Publication Data
US 2018/0344273 A1 Dec. 6, 2018

Related U.S. Application Data

(63) Continuation of application No. 15/065,071, filed on Mar. 9, 2016, now Pat. No. 10,028,713.

(51) Int. Cl.
*A61B 6/03* (2006.01)
*A61B 6/00* (2006.01)
*A61B 6/06* (2006.01)

(52) U.S. Cl.
CPC ............ *A61B 6/4441* (2013.01); *A61B 6/032* (2013.01); *A61B 6/035* (2013.01); *A61B 6/06* (2013.01); *A61B 6/4405* (2013.01); *A61B 6/4447* (2013.01); *A61B 6/466* (2013.01); *A61B 6/467* (2013.01)

(58) Field of Classification Search
CPC .......... A61B 6/032; A61B 6/035; A61B 6/06; A61B 6/4405; A61B 6/4441; A61B 6/4447; A61B 6/4466; A61B 6/467
See application file for complete search history.

(56) References Cited

U.S. PATENT DOCUMENTS

| | | | |
|---|---|---|---|
| 5,014,293 | A | 5/1991 | Boyd et al. |
| 6,203,196 | B1 | 3/2001 | Meyer et al. |
| 6,619,840 | B2 | 9/2003 | Rasche et al. |
| 6,940,941 | B2 | 9/2005 | Gregerson et al. |

(Continued)

FOREIGN PATENT DOCUMENTS

| | | |
|---|---|---|
| DE | 102006049574 A1 | 4/2008 |
| DE | 102011087718 A1 | 11/2012 |

(Continued)

OTHER PUBLICATIONS

International Preliminary Report on Patentability dated Sep. 20, 2018 in corresponding/related International Application No. PCT/US2017/021345.

(Continued)

*Primary Examiner* — Mark R Gaworecki
(74) *Attorney, Agent, or Firm* — Harness, Dickey & Pierce, P.L.C.

(57) ABSTRACT

A transformable imaging system configured to operate in at least two configurations. A first configuration may be open and a second configuration may be closed. The closed configuration may allow for imaging in along an arc greater than 180 degrees.

21 Claims, 21 Drawing Sheets

(56) References Cited

U.S. PATENT DOCUMENTS

| | | |
|---|---|---|
| 7,108,421 B2 | 9/2006 | Gregerson et al. |
| 8,303,181 B2 | 11/2012 | Sukovic et al. |
| 8,534,915 B2 | 9/2013 | Maschke |
| 8,662,750 B2 | 3/2014 | Maschke |
| 9,962,133 B2 | 5/2018 | Risher-Kelly et al. |
| 2007/0268540 A1 | 11/2007 | Gaspardo et al. |
| 2009/0312634 A1 | 12/2009 | Cora et al. |
| 2011/0122990 A1 | 5/2011 | Dafni |
| 2011/0316538 A1 | 12/2011 | Kim et al. |
| 2012/0200860 A1 | 8/2012 | Gaspardo et al. |
| 2015/0036799 A1 | 2/2015 | Zhang et al. |
| 2015/0114404 A1 | 4/2015 | Czop et al. |
| 2016/0015343 A1 | 1/2016 | Fortuna et al. |
| 2016/0015344 A1 | 1/2016 | Fortuna et al. |
| 2016/0038109 A1* | 2/2016 | Fortuna ............... A61B 6/4447 378/64 |
| 2017/0071685 A1 | 3/2017 | Crawford et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0258425 A1 | 9/2017 | Risher-Kelly et al. |
| 2017/0258426 A1 | 9/2017 | Risher-Kelly et al. |
| 2017/0258427 A1 | 9/2017 | Risher-Kelly et al. |

FOREIGN PATENT DOCUMENTS

| | | |
|---|---|---|
| WO | 03070101 A1 | 8/2003 |
| WO | 2014055488 A2 | 4/2014 |
| WO | 2017055488 A1 | 4/2017 |

OTHER PUBLICATIONS

Delta Tau Data Systems, Inc., Motion Control Systems Technical Notes "Gantry with Cross Coupling" Dec. 2015; 8 pages. Delta Tau's website: http://222.deltatau.com/dt_technicalnotes/technicalnotes.aspx.

International Search Report and Written Opinion dated Nov. 9, 2017 in corresponding/related International Application No. PCT/US2017/021345.

Invitation to Pay Additional Fees dated May 30, 2017 in corresponding International Application No. PCT/US2017/021345.

Office Action dated Apr. 4, 2019 in corresponding/related European Application No. 19150198.0.

Office Action dated Apr. 11, 2019 in corresponding/related European Application No. 19150199.8.

\* cited by examiner

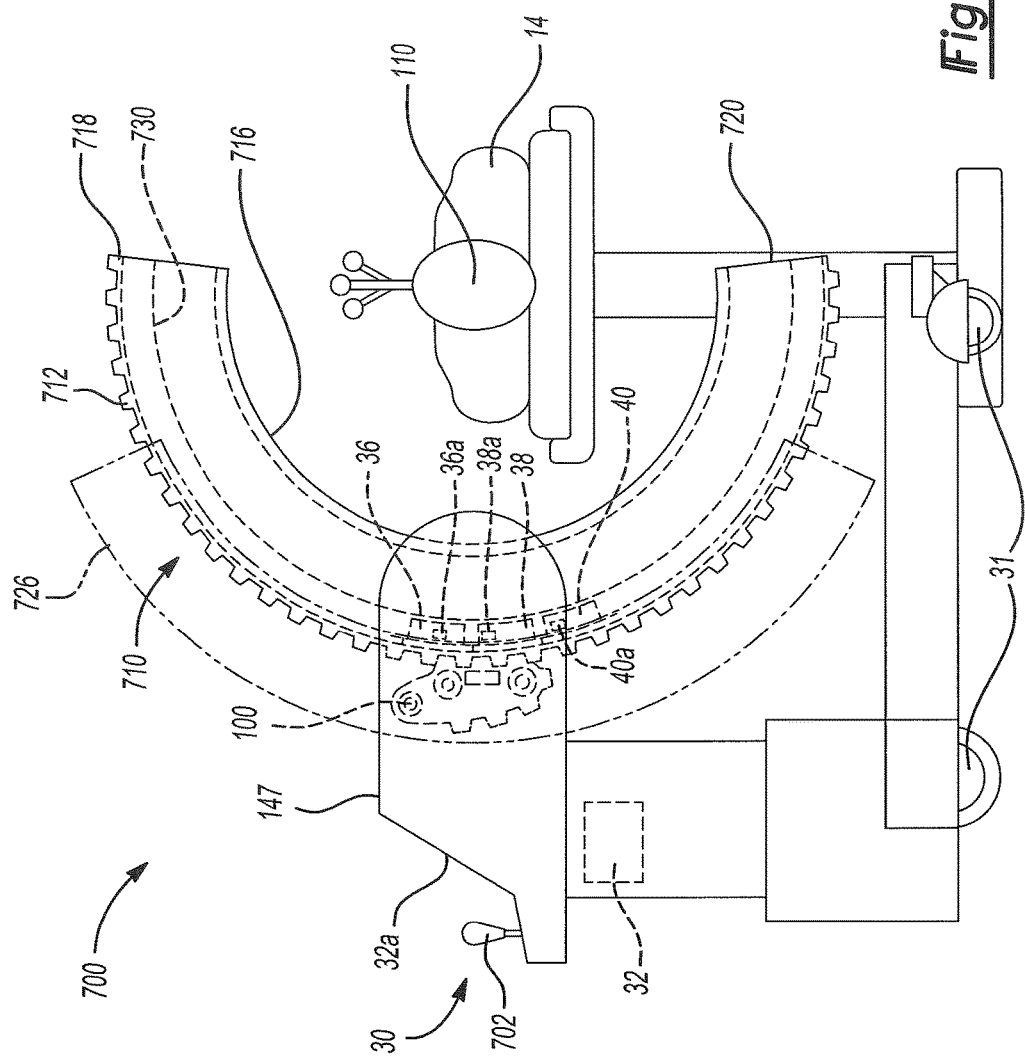

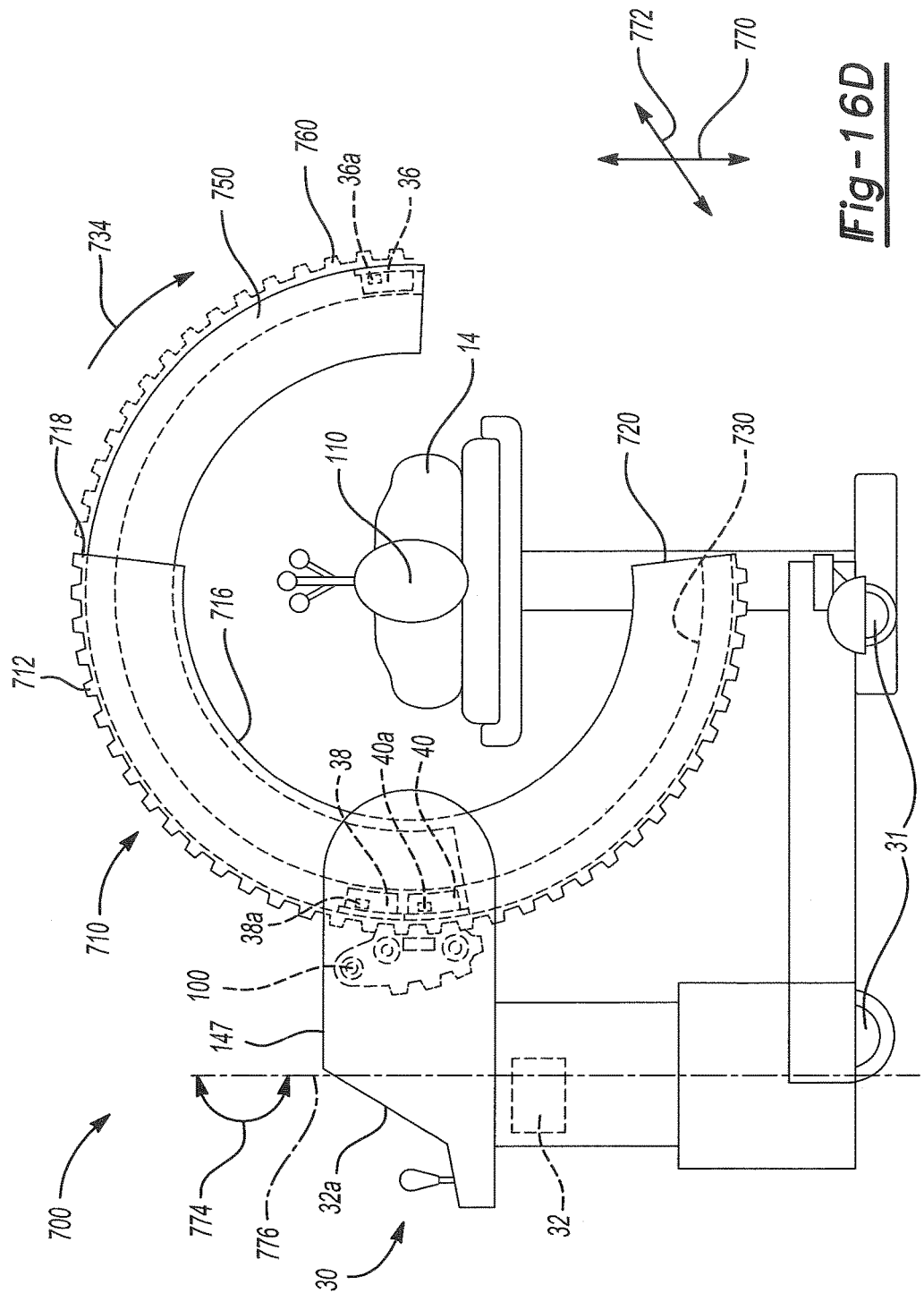

TRANSFORMABLE IMAGING SYSTEM

CROSS-REFERENCE TO RELATED APPLICATIONS

This application is a continuation of U.S. patent application Ser. No. 15/065,071 filed on Mar. 9, 2016. The entire disclosure of the above application is incorporated herein by reference.

The subject application includes subject matter similar to U.S. patent application Ser. No. 15/064,961 filed Mar. 9, 2016, and U.S. patent application Ser. No. 15/065,002 filed Mar. 9, 2016, both of which are incorporated herein by reference.

FIELD

The subject disclosure relates to imaging system, including a system to image an object via detection of transmitted radiation.

BACKGROUND

This section provides background information related to the present disclosure which is not necessarily prior art.

In performing various procedures, such as surgical procedures on a human patient, an imaging system may be used to image the patient. For example a fluoroscopic system may be used to emit x-rays from a source that is detected or received by a detector. Based upon the detection by the detector, images are generated of the patient. Certain systems are adapted for use during a procedure, such as the ARCADIAS Avantic® Multi-Purpose C-Arm Imaging System sold by Siemens Medical Solutions USA, Inc. having a place of business in Malvern, Pa., USA.

Generally, a C-Arm imaging system includes a source generally opposed to a detector on a "C" shaped or curved arm that is fixed. The arm extends along an arc where the source is near one end of the arm and the detector at the other end of the arm. The C-Arm may be moved relative to the patient to acquire images at different relative positions, such as an anterior to posterior and medial to lateral image perspectives. The arm, however, of the C-Arm, is generally a fixed arc dimension such that ends of the arm are fixed relative to one another based upon the geometry of the arm.

SUMMARY

This section provides a general summary of the disclosure, and is not a comprehensive disclosure of its full scope or all of its features.

According to various embodiments, an imaging system is provided that includes a source and a detector. The source may emit a radiation, such as x-ray radiation, that can be detected by the detector. An image may be generated based upon the amount of radiation reaching the detector. The amount of radiation may be attenuated by a portion of a subject in the path of the x-rays. The x-ray source and detector may be moved relative to a subject being imaged according to a changeable or transformable rotor that can assist in acquiring various types of image data.

A transformable imaging system can be used to efficiently acquire two dimensional image data based upon a single or limited number of subject exposures or three-dimensional (3D) volumetric image data based upon a plurality of exposures. For example, in a first configuration, an imaging system may have a "C" shaped arm that is less than annular and may acquire image data less than 360 degrees around the patient. These images may be best viewed or displayed as two dimensional images of a subject or may be used to generate 3D images of the subject. In a second configuration the imaging system may have an "O" shape or an annular shape and acquire image data substantially around, such as 360 degrees around, a subject based upon moving a detector and/or source through a path that is around or at a plurality of position relative to a subject. The annular or 360 degree acquisition of image data may allow for crisper or clearer 3D images for display.

According to various embodiments a system may include a configurable housing and/or rotor in and/or on which a detector and source may move. The detector and source may be operated in at least two manners based upon at least two configurations of the imaging system. Therefore a single system may be operable in two configurations to allow for versatility and flexibility of a single system.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 16A is an environmental view of an imaging system, according to various embodiments, with a source and detector located near each other;

FIG. 16D is an environmental view of an imaging system, according to various embodiments, with a source and detector located away each other and a moveable portion of the gantry extended in an extended "C"-shape;

Corresponding reference numerals indicate corresponding parts throughout the several views of the drawings.

DETAILED DESCRIPTION

Figure 1:
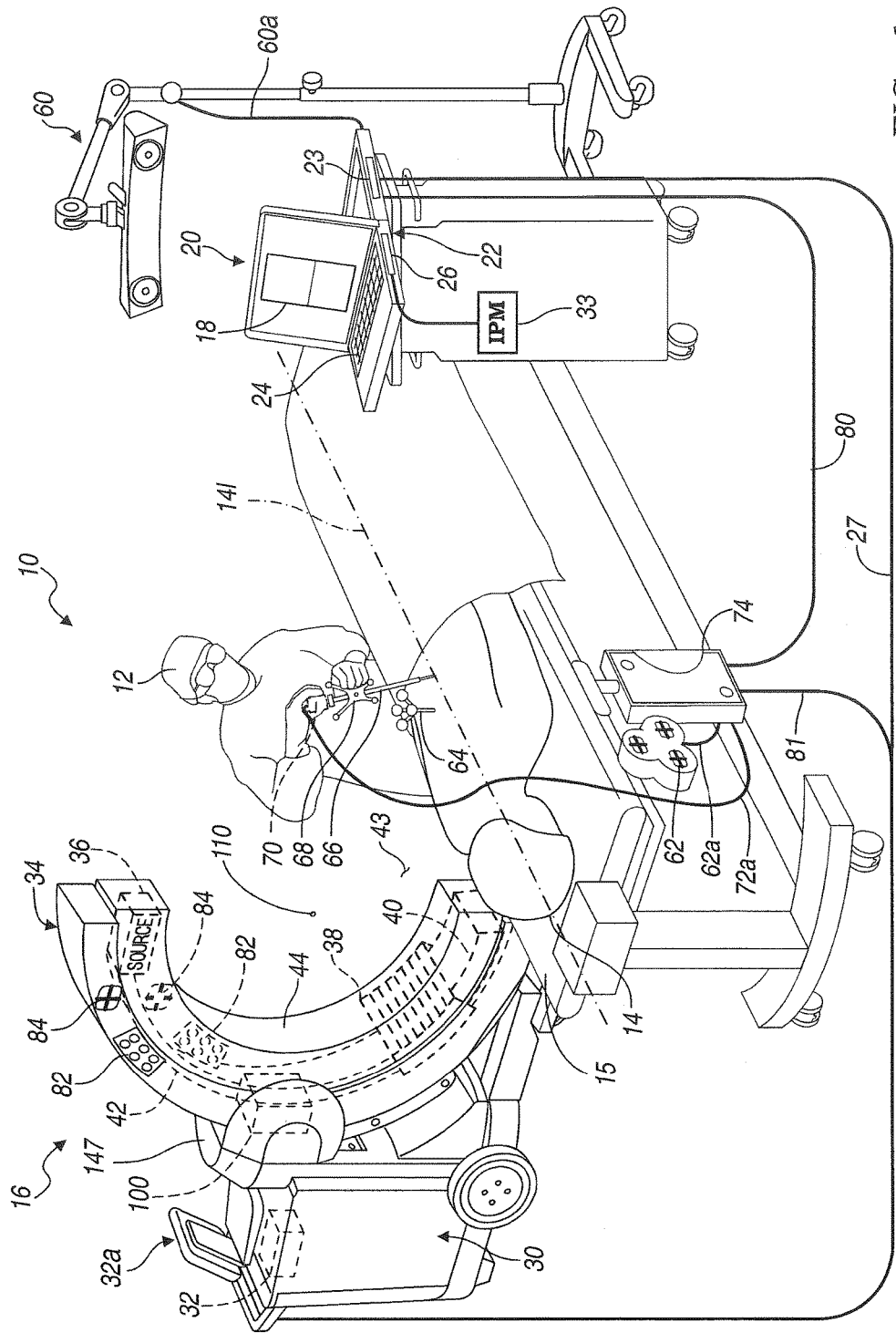
FIG. 1 is an environmental view of at least a portion of a suite including an imaging system in a first configuration, a tracking system, and a navigation system in accordance with an embodiment of the present disclosure.

The following description is merely exemplary in nature. It should be understood that throughout the drawings, corresponding reference numerals indicate like or corresponding parts and features. The present teachings are directed toward an imaging and a navigation system that is able to track an instrument and display it on a display. It is understood, however, that the systems disclosed herein may be applied to non-surgical applications for imaging, tracking, navigation, etc. during various repair or maintenance procedures on machinery, devices, etc.

Moving Sidewall Segmented Gantry

FIG. 1 shows an operating theatre (or inside of an operating room) 10 and a user 12 (e.g., a physician) performing a procedure on a subject (e.g., a patient) 14 positioned on a table or surface 15. In performing the procedure, the user 12 may use an imaging system 16 to acquire image data of the patient 14. The image data acquired of the patient 14 can include two-dimensional (2D) such as in a C-arm mode or three-dimensional (3D) images such as in a computer tomography (CT) mode. Models, such as surface renderings or volumetric models, may be generated using the acquired image data. The model can be a three-dimensional (3D) volumetric model generated based on the acquired image data using various techniques, including algebraic iterative techniques. The image data (designated 18) can be displayed on a display device 20, and additionally, may be displayed on a display device 32a associated with an imaging computing system 32. The displayed image data 18 may include 2D images, 3D images, and/or a time changing 3D (also referred to as 4D) images. The displayed image data 18 may also include acquired image data, generated image data, and/or a combination of the acquired and generated image data.

Image data acquired of a patient 14 may be acquired as 2D projections. The 2D projections may then be used to reconstruct 3D volumetric image data of the patient 14, such as when a selected number of differing perspective images are acquired of the patient 14. Also, theoretical or forward 2D projections may be generated from the 3D volumetric image data. Accordingly, image data may be used to provide 2D projections and/or 3D volumetric models.

The display device 20 may be part of a computing system 22. The computing system 22 may include a memory system 23 including one or a variety of computer-readable media. The computer-readable media may be any available media that is accessed by the computing system 22 and may include both volatile and non-volatile media, and removable and non-removable media. By way of example, the computer-readable media may include computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors may include multiple-processing core processors, microprocessors, etc.) that may be incorporated with the computing system 22. The input device 24 may include any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 may include a touchpad or tablet computing device and may be integrated within or be part of the imaging computing system 32. A connection may be provided between the computing system 22 and the display device 20 for data communication to allow driving the display device 20 to illustrate the image data 18. Further, a communication line 27 may be provided between the imaging computer system 32 and the computer system 22.

The imaging system 16 will be described in further detail herein, but may include certain portions included in an O-Arm® imaging system. The O-Arm® imaging system can include the O-Arm® imaging system sold by Medtronic, Inc. having a place of business in Colorado, USA. The imaging system may further include, in various embodiments, certain and selected portions of the imaging systems described in U.S. Pat. App. Pub. Nos. 2012/0099768, 2012/0097178, 2014/0313193, and 2014/0314199 and/or U.S. Pat. Nos. 7,188,998; 7,108,421; 7,001,045; and 6,940,941, all of which are incorporated herein by reference.

In various embodiments, the imaging system 16 may include a mobile cart 30, the imaging computing system 32 and a gantry 34. The gantry 34 may include a member or fixed dimension element. The fixed dimension member 34 may have a height 34x at an upper surface or edge 34y' (such as a highest point on the fixed dimension member 34) that is a selected height above a surface 34y that supports the imaging system 30. The height may be about 4 feet (about 1.2 meters) to about 6 feet (about 1.8 meters), may be five feet (about 1.5 meters) or less, or may be selected such that a user that is five feet six inches (about 1.6 meters) tall may easily see over the fixed dimension member 34. The imaging system further include an x-ray source 36, a collimator (not shown), one or both of a multi-row detector 38 and a flat panel detector 40, and a rotor 42. With reference to FIG. 1, the mobile cart 30 may be moved from one operating theater or room to another and the gantry 34 may be moved relative to the mobile cart 30, as discussed further herein. This allows the imaging system 16 to be mobile and used for various procedures without requiring a capital expenditure or space dedicated to a fixed imaging system. Although the gantry 34 is shown as being mobile, the gantry 34 may not be connected to the mobile cart 30 and may be in a fixed position.

The gantry 34 may define an isocenter 110 of the imaging system 16. In this regard, a centerline C1 through the gantry 34 may pass through the isocenter or center of the imaging system 16. Generally, the patient 14 can be positioned along the centerline C1 of the gantry 34, such that a longitudinal axis 141 of the patient 14 is aligned with the isocenter of the imaging system 16.

The imaging computing system 32 may control the movement, positioning and adjustment of the multi-row detector 38, the flat panel detector 40 and the rotor 42 independently to enable image data acquisition via an image processing module 33 of the processor 26. The processed images may be displayed on the display device 20. The imaging system 16 may be precisely controlled by the imaging computing system 32 to move the source 36, collimator, the multi-row detector 38 and the flat panel detector 40 relative to the patient 14 to generate precise image data of the patient 14. It is understood, however, that the source 36, and the detectors 38, 40 may be fixed at selected positions relative to the rotor 42.

In addition, the imaging system 16 may be connected or in connection with the processor 26 via the connection 27 which includes a wired or wireless connection or physical media transfer from the imaging system 16 to the processor 26. Thus, image data collected with the imaging system 16 may also be transferred from the imaging computing system 32 to the computing system 22 for navigation, display, reconstruction, etc.

The imaging system 16 may also be used during an non-navigated or navigated procedure. In a navigated procedure, a localizer may be used to determine location of tracked members and portions. The tracked members and portions may include the patient 14, the imaging system 16, the user 12, tracked instruments (e.g. drills, awls, probes), etc. The localizer may be one or both of an optical localizer 60 or an electromagnetic localizer 62. The localizer may further include an ultrasound localizer, a radar localizer, etc. The localizer may be used to generate a field or receive or send a signal within a navigation domain relative to the patient 14. If desired, the components associated with performing a navigated procedure (e.g. the localizer) may be integrated with the imaging system 16. The navigated space or navigational domain relative to the patient 14 may be registered to the image data 18 to allow registration of a navigation space defined within the navigational domain and an image space defined by the image data 18. A patient tracker (or a dynamic reference frame) 64 may be connected to the patient 14 to allow for a dynamic registration and maintenance of the registration of the patient 14 to the image data 18. It is understood, however, that imaging systems are not required to be used with a navigation or tracking system. Imaging systems, including those disclosed herein, may be used for imaging and evaluation of image data with navigation.

One or more instruments may be tracked within the navigational domain, including relative to the patient 14. Instruments may include an instrument 66 that may then be tracked relative to the patient 14 to allow for a navigated procedure. The instrument 66 may include respective optical tracking devices 68 (including active or passive tracking devices, including those discussed herein) and/or an electromagnetic tracking device 70 (shown in phantom) to allow for tracking of the instrument 66 with either or both of the optical localizer 60 or the electromagnetic localizer 62. The instrument 66 may include a communication line 72a with a navigation interface device (NID) 74. The NID 74 may communicate with the electromagnetic localizer 62 and/or the optical localizer 60 directly or via the processor 26 via communication lines 60a and 62a respectively. The NID 74 may communicate with the processor 26 via a communication line 80. The imaging system 16 may also communicate with the NID 74 via a communication line 81. The connections or communication lines can be wire based as shown or the corresponding devices may communicate wirelessly with each other.

The localizer 60 and/or 62 along with the selected tracking devices may be part of a tracking system that tracks the instrument 66 relative to the patient 14 to allow for illustration of the tracked location of the instrument 66 relative to the image data 18 for performing a procedure. The tracking system alone or in combination with a navigation system is configured to illustrate a tracked location (including a tracked 3D position (i.e. x,y,z coordinates) and one or more degrees of freedom of orientation (i.e. yaw, pitch, and roll)) relative to the image data 18 on the display 20. Various tracking and navigation systems include the StealthStation® surgical navigation system sold by Medtronic, Inc. and those disclosed in U.S. Pat. Nos. 8,644,907; 8,467,853; 7,996,064; 7,835,778; 7,763,035; 6,747,539; and 6,374,134, all incorporated herein by reference. As is generally understood, the processor 26 may execute selected instructions to illustrate a representation (e.g. an icon) of the tracked portion relative to the image data 18.

The instrument 66 may be interventional instruments and/or implants. Implants may include a ventricular or vascular stent, a spinal implant, neurological stent or the like. The instrument 66 may be an interventional instrument such as a deep brain or neurological stimulator, an ablation device, or other appropriate instrument. Tracking the instrument 66 allow for viewing the location of the instrument 66 relative to the patient 14 with use of the registered image data 18 and without direct viewing of the instrument 66 within the patient 14. For example, the instrument 66 may be graphically illustrated as an icon, as discussed further herein, superimposed on the image data 18.

Further, the imaging system 16 may include a tracking device, such as an optical tracking device 82 or an electromagnetic tracking device 84 to be tracked with a respective optical localizer 60 or the electromagnetic localizer 62. The tracking devices 82, 84 may be associated directly with the source 36, multi-row detector 38, flat panel detector 40, rotor 42, the gantry 34, or other appropriate part of the imaging system 16 to determine the location of the source 36, multi-row detector 38, flat panel detector 40, rotor 42 and/or gantry 34 relative to a selected reference frame. As illustrated, the tracking devices 82, 84 may be positioned on the exterior of the housing of the gantry 34. Accordingly, portions of the imaging system 16 may be tracked relative to the patient 14 to allow for initial registration, automatic registration, or continued registration of the patient 14 relative to the image data 18. The known position of the rotor 42 relative to the gantry 34, on which the tracking devise are placed, may be used to determine the position of the rotor 42 and the include detectors 38, 40 and source 36.

Alternatively, or in addition thereto, the tracking devices may be placed directly on the rotor 42 and/or the source 36 and detector 38, 40.

As discussed above, the user 12 can perform a procedure on the patient 14. The user 12 may position the instrument 66 relative to, such as within, the patient 14. For example, the instrument 66 can include an awl, tap, a probe, a screwdriver, an instrument to hold or position one or more screws, a rod, or the light. The instrument 66 may be tracked, as discussed above, and the location determined relative to the patient 14 and/or the imaging system 16.

An operative or operating portion (which may be a detachable portion) of the instrument 66 may be positioned subdermally and transdermally. In various embodiments, the portion of the instrument 66 positioned subdermally are positioned through a small incision or stab wound formed on or in the patient 14. Therefore, direct viewing, such as with visual viewing directly by the user 12 may be substantially hindered and/or impossible due to the overlayment of soft tissue including dermis, muscle, and the like. Therefore, the tracking and navigation systems, as discussed above, can be used to display representations of the instrument 66 relative to the image data 18 on display 20.

Figure 2:
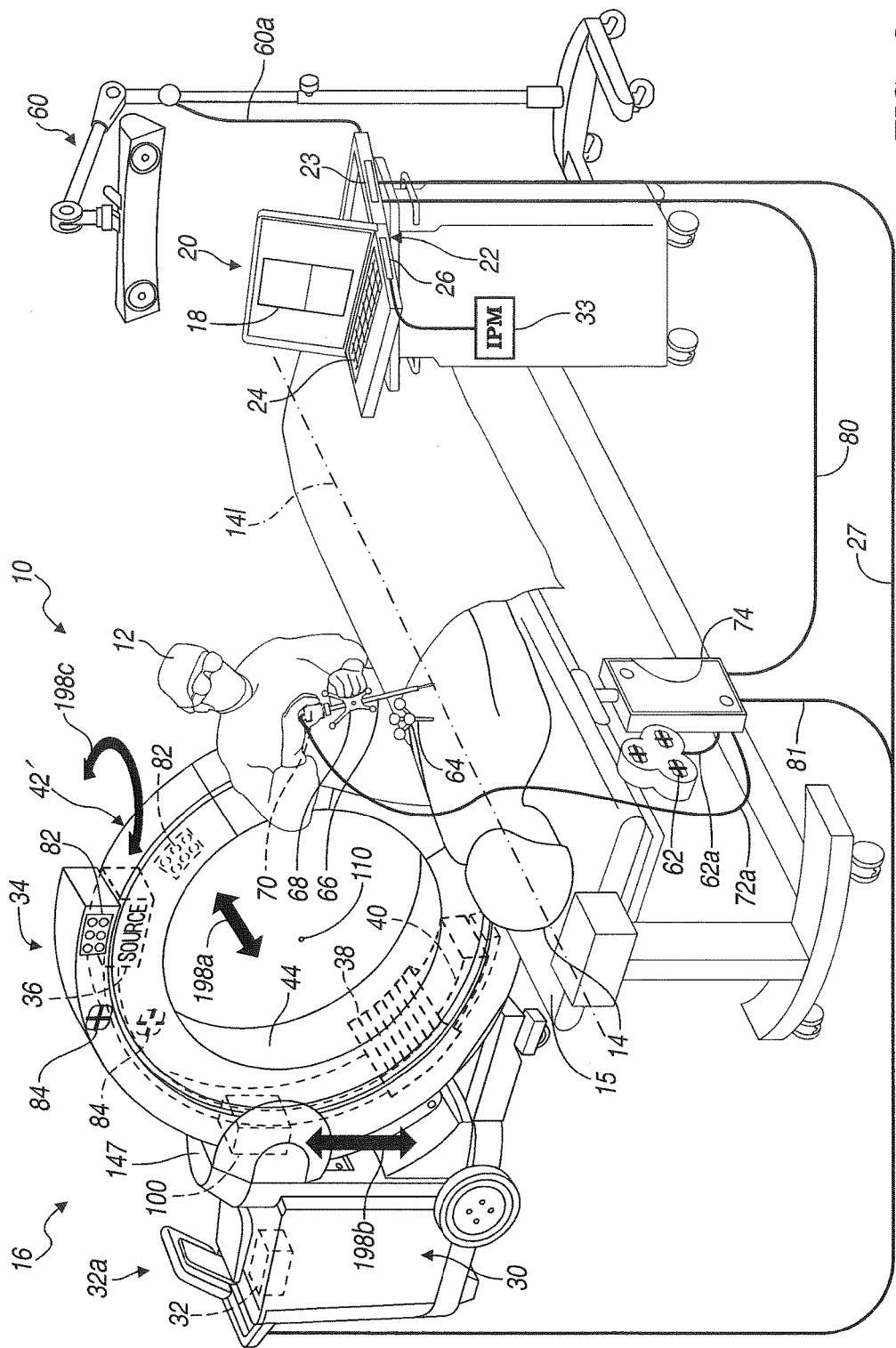
FIG. 2 is an environmental view of at least a portion of a suite including the imaging system in a second configuration, a tracking system, and a navigation system in accordance with an embodiment of the present disclosure.
Figure 9:
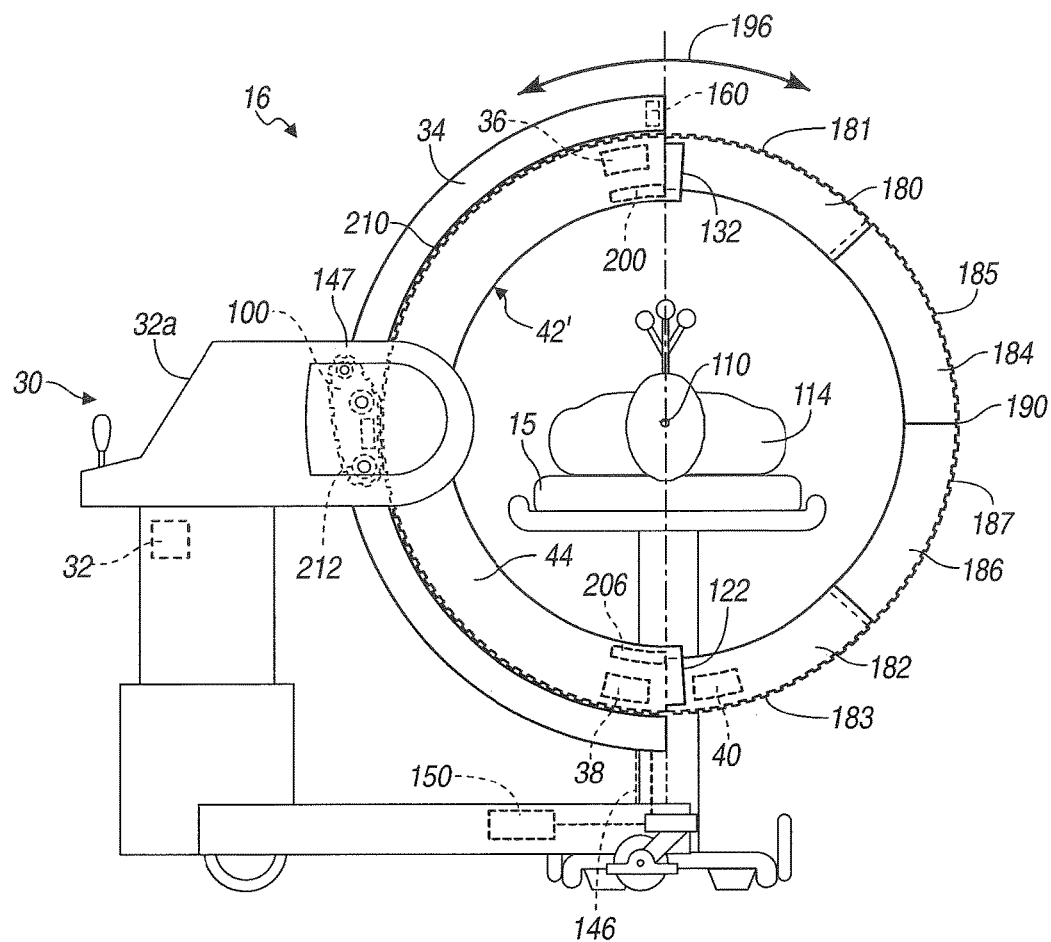

With continuing reference to FIG. 1, the operating theater can include the imaging system 16 that includes a transformable portion that may change configuration based upon a selected instruction. The transformable or multiple configurable imaging system 16 may include the rotor 42 having at least a fixed length portion or segment 44 in a "C" shape configuration, as illustrated in FIG. 1 or the rotor portion in an "O" shape configuration rotor 42', as illustrated in FIG. 2. The imaging system 16 when in the "C" shaped configuration may not enclose a circle and includes an opening 43 that is a side opening or laterally from an outside of the rotor 42. When the imaging system is in the "C" shape configuration rotor 42 it may operate as a C-arm. The opening 43 allows access to the patient 14 from the user 12 even when the imaging system 16 is near the patient 14. A complete circle (as illustrated in FIG. 9) does not allow side access to the patient 14 through the "O" shape configuration rotor 42'.

The moveable rotor 42 may move relative to the gantry 34, as discussed herein. The gantry 34 may have a fixed configuration and the rotor 42 moves relative to the gantry 34 due to coupling of a rotor drive system 100, as discussed further herein, to allow for movement of the rotor 42 relative to the gantry 34. The drive system 100 can be operated by the computer system 32, as also discussed further herein.

Turning reference to FIG. 2 the imaging system 16 can be transformed or configured to include the "O" shaped configuration rotor 42'. The "O" shaped configuration rotor 42' does not include the side opening 43, but includes a substantially annular configuration. When the imaging system 16 is in the "O" shaped configuration rotor 42' it may be operated as a CT mode or as the O-Arm® imaging system. The rotor drive 100 may still be operated to move the "O" shaped configuration rotor 42' relative to the gantry 34, but the "O" shaped configuration rotor 42' may move in at least a 360° circle around the subject 14 that may be placed within the "O" shaped configuration rotor 42'. The subject 14 may be placed within the annular portion of the "O" shaped configuration rotor 42' by first having the "C" shaped configuration rotor 42, as illustrated in FIG. 1, moved relative to the patient 14 and then changing or transforming the imaging system 16 to the "O" shaped configuration rotor 42', as illustrated in FIG. 2, as discussed further herein.

Returning reference to FIG. 1, the imagining system 16 in the "C" shaped configuration rotor 42 may operate as a conventional C-arm, including those discussed above. With additional reference to FIGS. 3-6, the imaging system 16 in the "C" shaped configuration rotor 42 can generally move at least 180° around an isocenter 110 using the rotor drive 100. The source 36 is positioned substantially opposed to the detector or plurality of detectors 38, 40. The source 36 may be positioned away from a base 112 of the cart or a floor.

Figure 4:
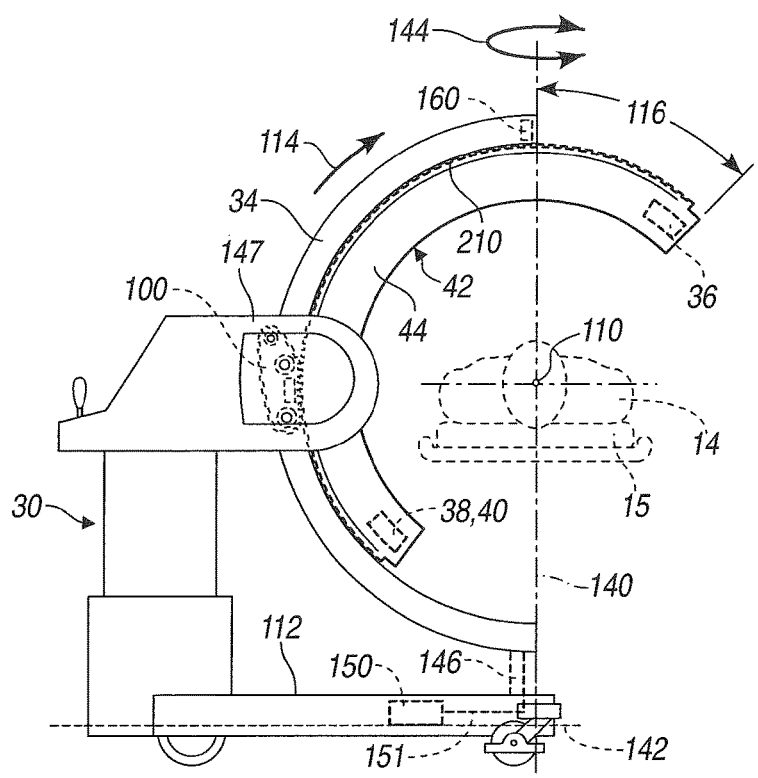

The "C" shaped configuration rotor 42 may be rotated generally in the direction of arrow 114 along a distance or arc length 116 relative to an end of the gantry 34. It is understood that the arc length 116 can be any appropriate arc length, and is illustrated in FIG. 4 as exemplary indicating a possible position or movement of the "C" shaped configuration rotor 42. The "C" shaped configuration rotor 42 may then continue to move generally in the direction of arrow 114 including an arc length distance 118 relative to an end of the gantry 34. The "C" shaped configuration rotor 42 may be held on the gantry 34 with an appropriate amount, such as a maintaining or connecting leg portion 120 that may extend between a first terminal end 122 and a stop point 124. It is understood that the holding portion 120 can be based on various considerations such as the rigidity or mass of the overhang length 130, weight of the "C" shaped configuration rotor 42, strength or rigidity of the gantry 34, and other considerations. Further, it is understood, that the arc length 118 may be selected based upon the position of the drive 100 and other mechanical and connections to allow for movement of the "C" shaped configuration rotor 42.

Figure 5:
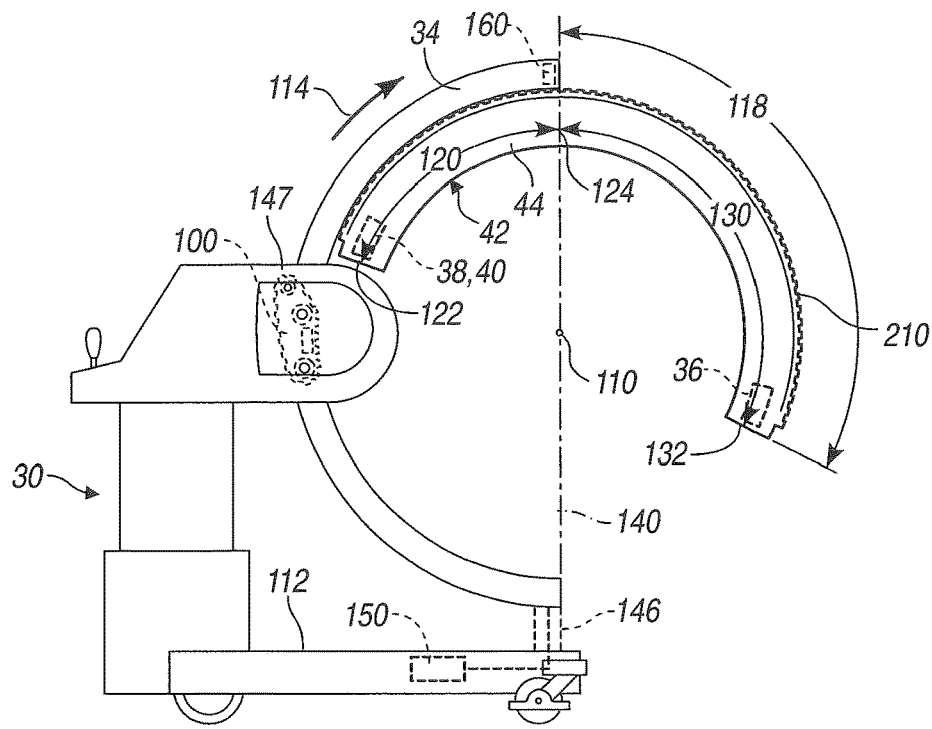
Figure 6:
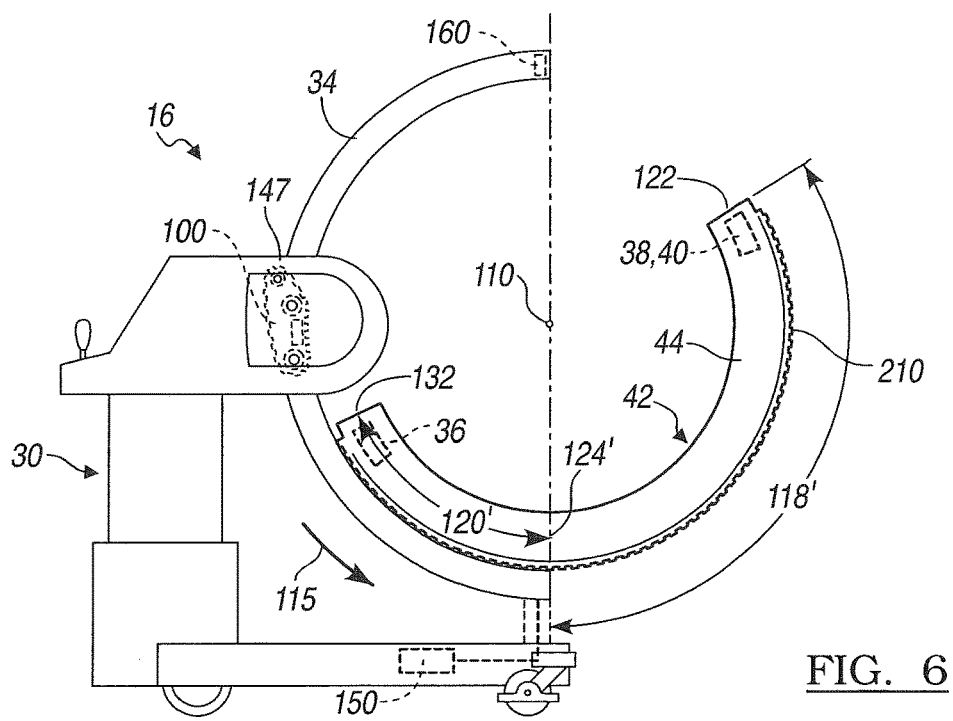

With specific reference to FIG. 6, the "C" shaped configuration rotor 42 may also rotate in a substantially opposite direction, such as in the direction of arrow 115, from that illustrated in FIG. 5. In moving in the direction of arrow 115, the first terminal end 122 extends away from the gantry 34. The first terminal end 122 may also be moved an arc length 118' that may be substantially equal in length to arc length 118. Further an overhang or connecting length 120' may be the distance between a minimal overhang or contact point 124' and a second terminal end 132 of the "C" shaped configuration rotor 42.

Accordingly, it is understood that the "C" shaped configuration rotor 42 may move relative to the gantry 34 of the imaging system 16 a selected or maximum amount of movement. Generally the movement may be about 180°, such that allowing the detector 38, 40 to move at least 180° around the isocenter 110 at which the patient 14 may be positioned. In other words, the movement of the detector 38, 40 may be limited to about 180° of total movement around the isocenter 110. It is further understood, however, that the detector 38, 40 may move less than or greater than 180°, including about 150° to about 270° around the isocenter 110.

With continuing reference to FIGS. 1 and 3-6, the imagining system 16 in the "C" shaped configuration rotor 42 that includes the open space 43, can be operated in a manner substantially similar to a generally known C-arm. In the "C" shaped configuration rotor 42, generally fluoroscopic images or two dimensional (2D) images may be acquired of the patient 14. The two dimensional or fluoroscopic images may be used to efficiently acquire image data the patient 14 during an operative procedure, as illustrated in FIG. 1. The "C" shaped configuration rotor 42 including the opening 43 may also allow for an efficient movement of the imaging system 16 relative to the subject 14.

Further, the opening 43 may allow easy access to the patient 14 during imaging to allow the user 12 to perform a procedure with the imaging system 16 positioned relative to the patient 14, such as in a position to acquire intra-operative images of the patient 14. Thus, the opening 43 may assist the user 12 in performing a procedure on the patient 14 by allowing the user 12 to acquire intra-operative images data for viewing on the display 20. The image data 18 can be used to update the user 12 regarding the procedure, including confirmation of a procedure, positioning of an implant, or other portions thereof.

According to various embodiments, the user 12 may access the patient 14 while the patient is at the isocenter 110 of the imaging system 16 through the side opening 43. Thus, the user 12 may image the patient 14 during the procedure to assist in the procedure, such as implant placement. The imaging system 16, therefore, need not be removed during a procedure. Also, as discussed herein, the imaging system 16 may be transformed into the "O" shaped configuration rotor 42' to acquire additional image data, such as image data for a 3D image of the patient 14. The single imaging system may provide the user 12 with different types of image data at different times without requiring separate imaging systems.

In addition to rotating generally along a path defined by the gantry 34, the "C" shaped configuration rotor 42 may move or pivot around an axis 140 that may extend generally perpendicular to the long axis 142 (as illustrated in FIG. 4) of the base 112 or the axis 141 of the patient 14. Further, the long axis 142 may be generally parallel to the floor or support surface on which the imaging system 16 is placed. The central axis 140 may allow for a swivel or rotation around the patient 14 generally in the direction of arrow 144. Alternatively, or in addition possible motions of the imaging system are also illustrated in FIG. 4A as discussed herein.

The movement around the axis 140 in the direction of arrow 144 may be allowed by a spindle or axle 146 that extends from the base 112 and is driven by a gantry drive 150 via a coupling 151. Thus, the gantry may rotate around the axle 146 allowing the "C" shaped configuration rotor 42 to also rotate. Further, the gantry 34 may also be moved with a connection 147, similar to the gantry movement systems discussed above and including in the O-Arm® imaging system. The gantry drive 150 may then be coupled to the connection 147. The gantry drive 150 may be similar to the rotor drive 100, discussed above, and further herein, or any appropriate drive including worm gear, a hydraulic system, a pneumatic system, an electrical motor, a serpentine belt drive, or other appropriate drive or connection system.

Figure 4A:
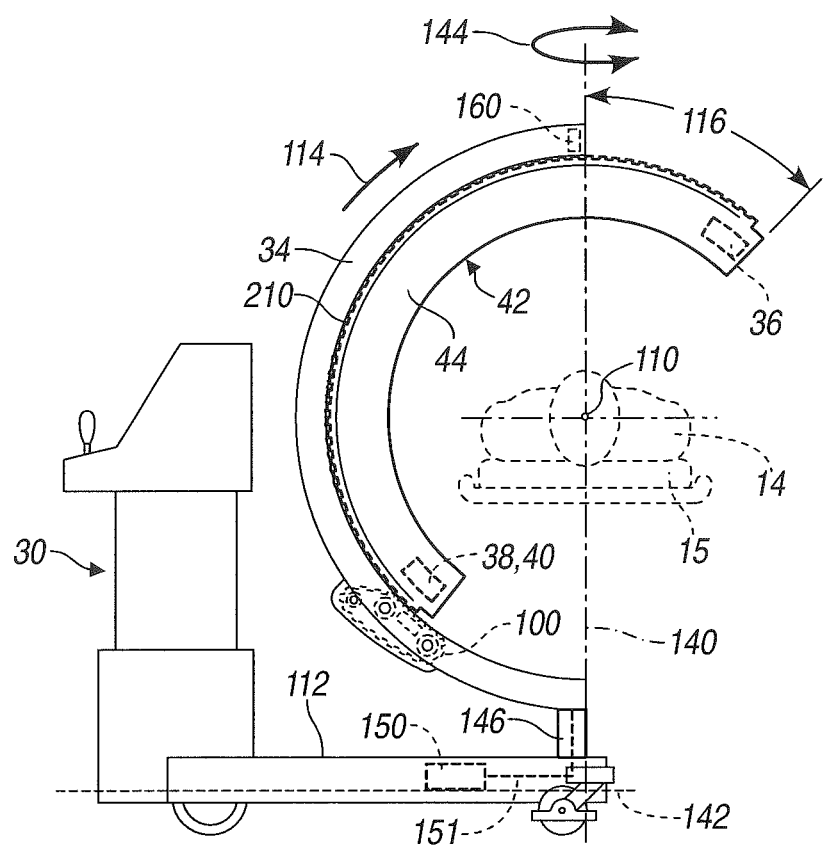

It is understood, as illustrated in FIG. 4A, that the connection 147 may be eliminated or moved to allow for the rotation in the direction of arrow 144. The connection 147 may allow for other movements, as discussed herein, but may restrict a rotation around the axis 140. Thus, the axle 146 may interconnect the gantry 34 and the base 112 to allow for rotation of the gantry 34 around the axis 140. The drive 100, therefore, may be moved relative to the base 112 and be connected (e.g. with a belt) to the gantry 34 and/or rotator 42 for movement of the rotor 42.

Alternatively, or in addition to the axle 146, the "C" shaped configuration rotor 42 may rotate relative to the gantry 34 by interconnection with an axle 160 that extends from the gantry 34 and engages the moveable rotor 42, such as via a recess track or other appropriate connection. Therefore the gantry 34 may be fixed relative to the base 112 while the rotor 42 rotates relative to the gantry 34. The amount of rotation generally in direction of arrow 144 may be selected or limited to a configuration of the imaging system 16. The rotation, however, may include about 180° rotation around the axis 140.

Further, the gantry may also move in selected movements relative to the cart 30, including the base 112. As discussed herein, the gantry may move independent of the "C" shaped configuration rotor 42 via the axle 146 or the connection 147. The movements may allow for iso-sway, linear translation, etc. of the gantry to further move the "C" shaped configuration rotor 42.

Figure 3:
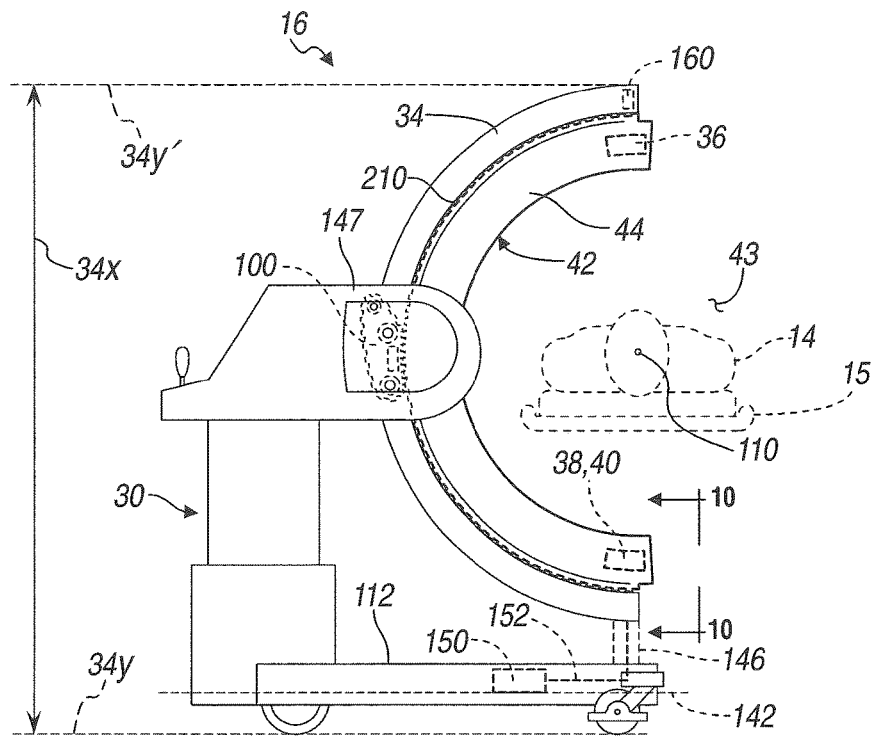
FIGS. 3 to 6 illustrate schematic views of the imaging system in the first configuration in a series of positions.
Figure 7:
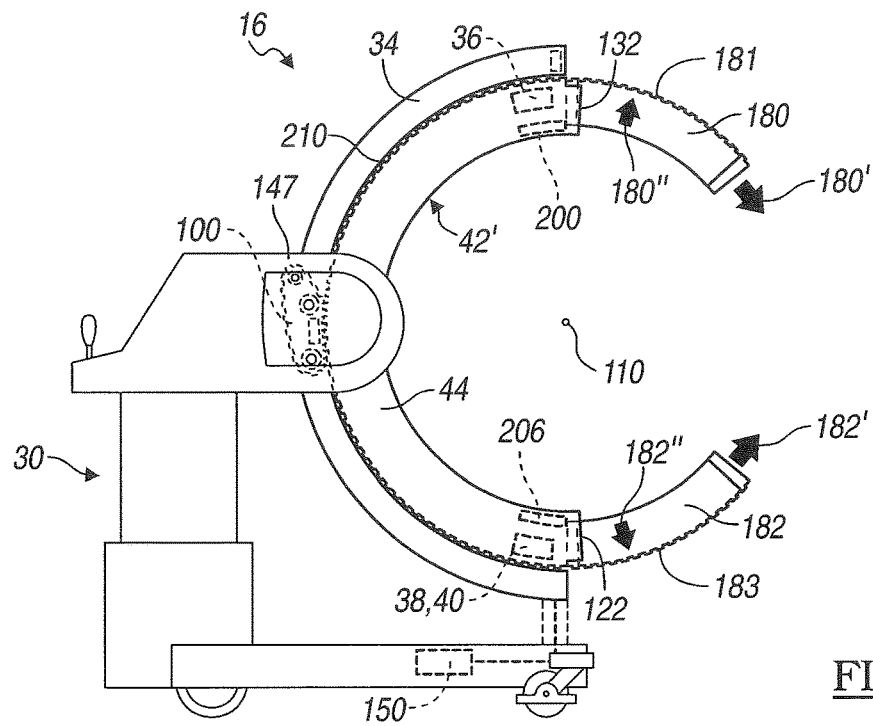
FIGS. 7 to 9 illustrate schematic views of the imaging system changing from the first configuration to the second configuration in a series of positions.
Figure 8:
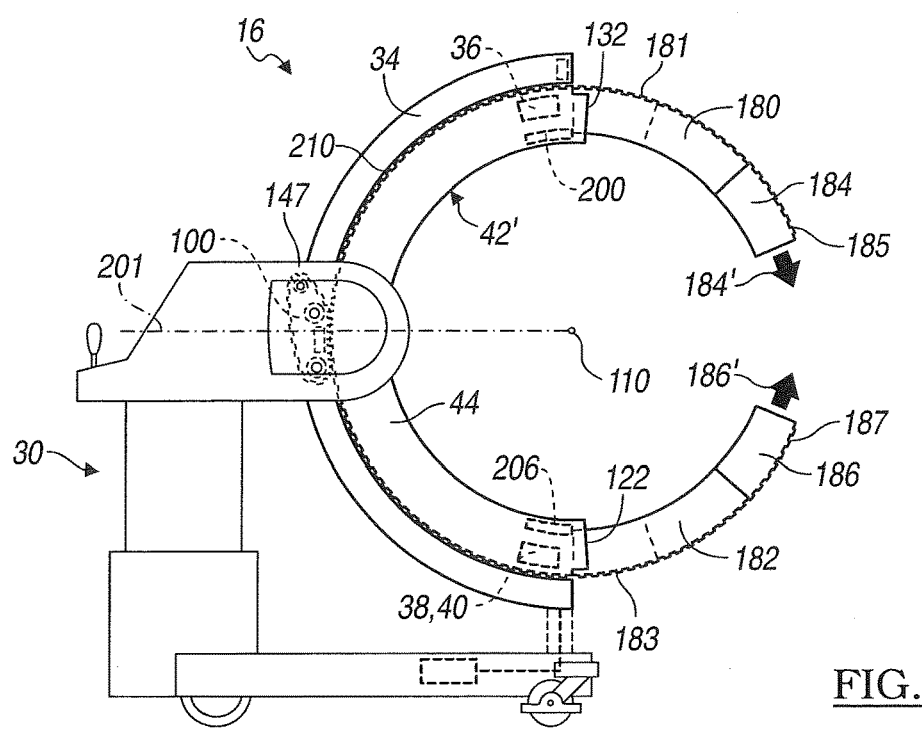

Returning reference to FIG. 2 and additional reference to FIGS. 7-9, the imaging system 16 may be transformed or reconfigured to include the "O" shaped configuration rotor 42', is illustrated in FIG. 2 and FIG. 9. The imaging system 16 including the "C" shaped configuration rotor 42, as illustrated in FIG. 3. As discussed herein, one or more moveable segments may move to change the "C" shaped rotor 42 to the "O" shaped rotor 42'. Various exemplary embodiments of the moveable segments are discussed herein.

The "C" shaped configuration rotor 42 when changing to the "O" shaped configuration rotor 42' can include intermediate shapes, such as one or two intermediate shapes, as generally illustrated in FIGS. 7 and 8. For example the "C" shaped configuration rotor 42 may include a first moveable segment 180 and a second moveable segment 182. The first and second moveable segments 180, 182 can extend from the respective terminal ends 132 and 122 of the "C" shaped configuration rotor 42. The moveable segments 180, 182 may be held or stored within the "C" shaped configuration rotor 42 when the "C" shaped configuration rotor 42 is in the "C" shaped configuration, as illustrated in FIG. 3, and extends when a command is provided to move the moveable segments 180, 182 to form the "O" shaped configuration rotor 42'.

A drive 200 and/or a drive 206 may be provided to move the moveable segments 180, 182. It is understood, however, that the drive 100 may also move the moveable segments 180, 182. The first and second moveable segments 180, 182 can extend from the respective terminal ends 132 and 122 of the "C" shaped configuration rotor 42 generally in the direction of arrows 180' and 182', respectively, as illustrated in FIG. 7. The moveable segments 180, 182 may also move generally radially outward or away from the isocenter 110 in the directions of arrows 180" and 182". The first moveable segment 180 includes an outer edge with teeth 181 and the second moveable segment includes a second outer edge with teeth 183. The movement of the moveable segments 180, 182 allows for the outer edges to be aligned with the outer edge of the fixed length segment 44.

Further, as illustrated in FIG. 8, a third moveable segment 184 can extend from the first moveable segment 180 and a fourth moveable segment 186 can extend from the second moveable segment 182 by being driven by the drives 100, 200, and/or 206 as described above. The third moveable segment may also move in an arc along arrow 184' and radially in the direction of arrow 184". Further, the fourth moveable segment 186 may move in an arc along arrow 186' and radially in the direction of arrow 186", similar to the movements described above. These movements allow respective outer edges with teeth 185 and 187 to be aligned with the outer edge of the fixed length segment 44. The third and fourth moveable segments 184, 186 can then meet or join at a joint region 190, as illustrated in FIG. 9.

Each of the moveable segments 180, 182, 184, 186 can be held or stored within the "C" shaped configuration rotor 42 and extend therefrom upon a command by a user, such as the user 12, to reconfigure the imaging system 16 into the "O" shaped configuration rotor 42'. The movements of the segments 180, 182, 184, 186 can be in the appropriate manner, including those discussed further herein.

As illustrated in FIG. 2 and FIG. 9, the "O" shaped configuration rotor 42' can extend annularly, generally about 360 degrees, around the isocenter 110 at which the patient 14 may also be placed. The patient 14 may be placed on the table 15 to be imaged with the "O" shaped configuration rotor 42' by moving the imaging system 16 near or adjacent to the table 15 with the patient 14 placed when the imaging system is in the "C" shaped configuration rotor 42. After moving the imaging system to have the patient 14 at a selected relative location, e.g. at the isocenter 110, the command can be entered (e.g. with the input 24 or directly to the imaging computer 32) to reconfigure the imaging system 16 to the "O" shaped configuration rotor 42'. The "O" shaped configuration rotor 42' can then rotate around the patient 14, including around the long axis 141 of the patient 14. The long axis 141 (as illustrated in FIG. 1) of the patient 14 may generally be placed such that it intersects the isocenter 110 of the imaging system 16. The rotation of the "O" shaped configuration rotor 42' can be generally in the direction of arrow 196 around the long axis 141 and the isocenter 110.

It is understood, however, that the "O" shaped configuration rotor 42', as illustrated in FIG. 2 and FIG. 9, may also move relative to the isocenter 110 in other movements. For example the gantry 34 may be moved relative to the isocenter 110 linearly along the long axis 141, such as generally in the direction of arrow 198*a*. The gantry 34 also may be moved generally perpendicular to the long axis 141 generally in direction of arrow 198*b*. Still further, the gantry 34 may also be moved angularly relative to the long axis generally in the direction of arrow 198*c*, all is illustrated in FIG. 2. The movements of the gantry 34 may be with the gantry drive 150, discussed above, and due to the connections of the axle 146 or the connection 147.

When the imaging system 16 has been reconfigured to the "O" shaped configuration rotor 42' the source 36 and the detectors 38, 40 can move generally in a path relative to the patient 14. The path may be at least 360° around the patient to acquire image data substantially in an entire circle 360° round the patient 14. The path of the detector 38, 40, however, need not be circular and may be spiral, less than a circle, or travel over a portion of path previously completed to acquire image data. The path may be defined by movements of the rotor 42 and/or the gantry 34. In acquiring the image data around the patient 14, such as 360°, a volumetric reconstruction can be made of the patient 14 using the image data acquired around the patient. The image data acquired and the reconstruction thereof can be known according to various techniques including those disclosed in U.S. Pat. App. Pub. Nos. 2012/0099768, 2012/0097178, 2014/0313193, and 2014/0314199 all incorporated herein by reference. For example, the image data can be acquired at the plurality of the angles relative to the patient 14 to identify or determine the geometry of the structures being in imaged. Nevertheless, when the imaging system 16 is in the "O" shaped configuration rotor 42' the patient 14 can be imaged substantially completely angularly around the patient 14.

Accordingly, as illustrated above, the imaging system 16 may be configurable between the "C" shaped configuration rotor 42, as illustrated in FIG. 1, and the "O" shaped configuration rotor 42', as illustrated in FIG. 2. This can allow the imaging system 16 to acquire image data according to different techniques while allowing the user 12 to access the patient 14 during an operative procedure. As discussed above, when in the "C" shaped configuration rotor 42 the user 12 may have substantially free access to the patient 14 through the opening 43, as illustrated in FIG. 3. However, if it is desired or selected to acquire image data for a more complete volumetric reconstruction, the imaging system 16 can be reconfigured to include the "O" shaped configuration rotor 42' as illustrated in FIGS. 2 and 9.

With continued reference to FIGS. 7-10B, the drive 200 of the imaging system 16 may be coupled between the fixed length segment 44 of the rotor 42 and the moveable segments 180, 182, 184, 186. The drive 200 can operably move the segments 180, 182, 184, 186 to reconfigure the imaging system between the "C" shaped configuration rotor 42 and the "O" shaped configuration rotor 42'. The drive 200 can be provided in various configurations or types including an electric motor, a hydraulic motor, a pulley and cable system driven by a selected motor, a pneumatic system, a belt drive system including a belt driven by the drive 200, or the like including linkages to the segments 180, 182, 184, 186. As discussed further herein the drive 200 can interconnect to the segments, such as the first segment 180, to move the first segment 180 relative to the fixed length segment or portion 44.

Figure 10A:
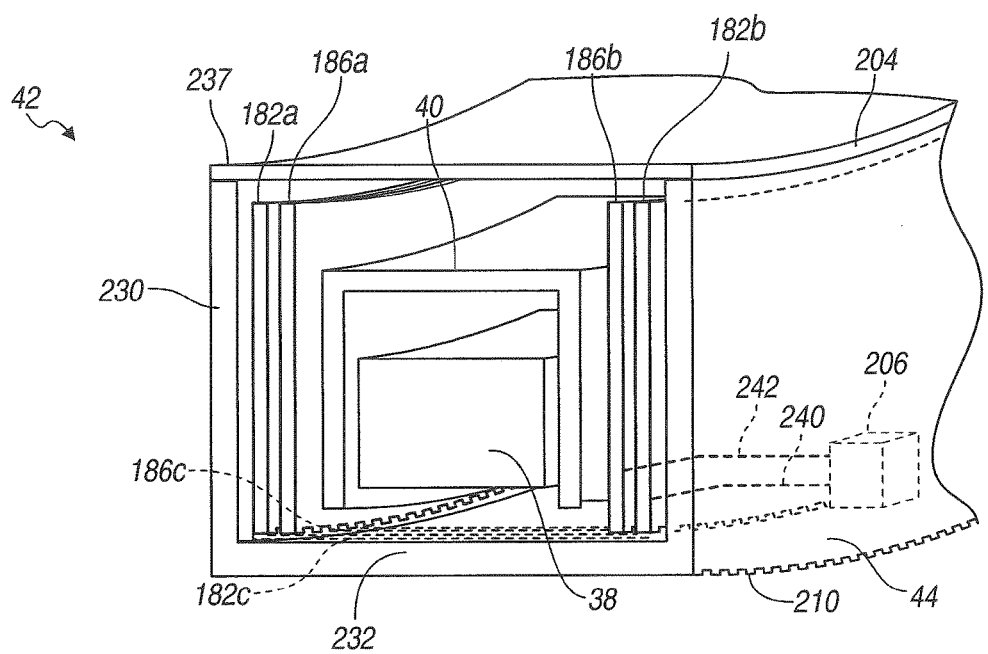
FIG. 10A is a detailed view taken from FIG. 3 with members in a first position.

As also discussed further herein the first segment 180 can be moved to a position within an internal wall 204, as illustrated in FIG. 10A, of the fixed length portion 44. It is further understood that various linkages, including rigid, flexible, and multi member linkages, may connect the fixed length segment 44 and the moveable segments 180, 182, 184, 186 to move the segments 180-186 relative to fixed length segment 44. Further an additional drive, including the drive 206 may be provided to engage a selected number of segments, including the second and fourth segments 182, 186 to move those segments relative to the fixed length segment 44 while the first drive 200 moves only the first and the third segments 180, 184. Further, it is understood that any appropriate number of the moveable segments may be provided, including less than the four or more than the four moveable segments 180, 182, 184, 186. Also, any selected number of the moveable segments may be provided to extend from only one end of the fixed length segment 44.

With continued reference to FIG. 9, the imaging system 16 includes the gantry 34 positioned or moveable relative to the cart 30. The cart 30 can include the portions as described above, including the computer 32 and the monitor 32*a*. The gantry 34 may have mounted thereon the drive 100 that can include various portions to engage the rotor 42, 42' to move the rotor 42, 42' relative to the gantry 34 and relative to the cart 32. According to various embodiments, the fixed length segment 44 may include an engageable portion, such as a tooth edge or a track 210 that can be engaged by a driver portion 212, which may include a belt or wheel. The driver portion 212 may include at least one tooth (not illustrated) to engage the tooth 210 of the track portion of the fixed length segment 44.

The movement of a motor of the drive 100, which may be driven by a motor, including an electric motor, a hydraulic motor, or other appropriate motor, can move the drive portion 212 to move the fixed length segment 44 as illustrated in FIGS. 4-6. Accordingly the source 36 and the detector 38, 40 can be moved relative to the patient 14 that is positioned within an opening of the fixed length segment 44. X-rays may be emitted from the emitter 36 and detected on the detector 38, 40 for generation of image data 18. The gantry 34 can also move relative to the cart 30, using the gantry drive 150, as discussed above, which may be an electrical drive system, a hydraulic drive system, or the like to move the gantry 34 relative to the patient 14. The gantry 34, therefore, may move relative to the cart 30 and the patient 14. As the fixed length segment 44 is connected to the gantry 34 the fixed length segment 44 may also move in these directions relative to the patient 14 and the cart 30 with the gantry 34.

With continued reference to FIG. 9, the segments 180, 182, 184, and 186 can extend from the fixed length segment 44 to form "O" shaped configuration rotor 42'. The moveable segments 180, 182, 184, and 186 include the external surfaces 181, 183, 185 and 187, respectively, that can be moved to be coextensive or extend from the tooth track 210 on the fixed length segment 44. As discussed above, the moveable segments may move in both arcuate or curved paths and linear paths (e.g. radially from center of the arc) to form a continuous track for the "O" shaped configuration rotor 42'. Accordingly when the segments 180, 182, 184, and 186 are extended from the fixed length segment 44 the tooth track 210 of the fixed length segment 44 can continue to substantially continuously and smoothly 360° in the "O" shaped configuration rotor 42' by connection with the exterior surfaces 181, 183, 185 and 187 of the segments 180, 182, 184, and 186. Therefore, the "O" shaped configuration rotor 42' can be driven by the drive 100 at least 360° around the patient 14 to acquire images of the patient 14.

Figure 10B:
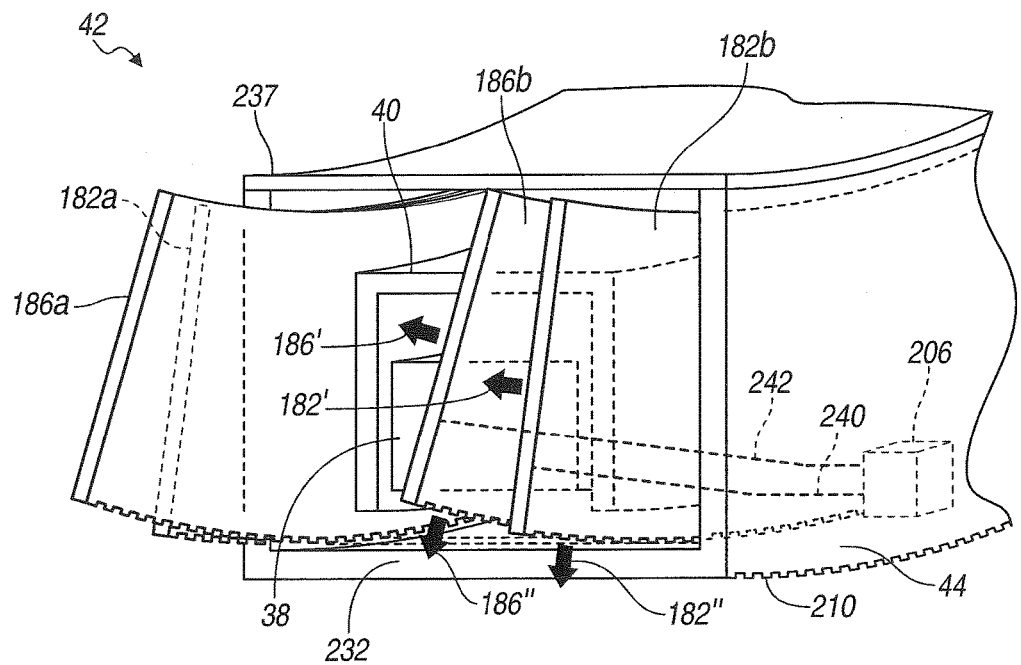
FIG. 10B is a perspective view of members illustrated in FIG. 10A in a second position.

The emitter 36 and the detectors 38, 40 can remain substantially relative to the fixed length segment 44 while the "O" shaped configuration rotor 42' rotates around the patient 14 to acquire the image data of the patient 14. In other words, the emitter 36 and the detector 38, 40 need not move relative to the fixed length segment 44 to achieve rotation or movement around the patient 14. Further, any or all of the emitter 36 and the detector 38, 40 may be placed between sidewalls of the fixed length segment 44, as illustrated in FIGS. 10A and 10B. Thus, when rotating the O" shaped configuration rotor 42' the patient is not substantially exposed to the emitter 36 and the detector 38, 40. A top wall may also be provided to further protect or shield the patient from the emitter 36 and the detector 38, 40.

The movement of the gantry 34, including either the fixed length segment 44 and the "C" shaped configuration rotor 42 or the "O" shaped configuration rotor 42', can be operated by a drive signal from the computer 32 to the drive 100. The drive signal can include a distance and speed of movement signal for gantry 34 and the rotor 42, 42' relative to the patient 14. Thus, the drive signal from the computer 32 can include movements generally along the arrows 198a, 198b, and 198c. The computer 32 can provide a drive signal to move the fixed gantry 34 and/or the rotation of the gantry 42, 42' to move the detector 38, 40 and/or emitter 36 relative to the patient 14. Possible drive scans can be provided by user 12 or other operators as disclosed in U.S. Patent application U.S. Pat. App. Pub. Nos. 2012/0099768, 2012/0097178, 2014/0313193, and 2014/0314199, all incorporated herein by reference.

With additional reference to FIGS. 10A and 10B, the rotor 42 including segments 182 and 186 are illustrated in cross section from FIG. 3. The fixed length segment 44 can include the first exterior wall 204 and a second exterior wall 230. The two exterior walls 204, 230 can be interconnected by a bottom or exterior wall 232 or a plurality of reinforcing struts or members. The drive track including the teeth 210 can be formed into at least one edge of the outer wall 232 or formed on one of the exterior walls 204, 230. The detectors 38, 40 may also be substantially confined or placed within a volume defined between the sidewalls 204, 230. The emitter 36 may also be similarly positioned opposed to the detectors 38, 40. An inner cover or inner annular wall 237 may also be provided to complete a volume within the fixed length segment 44 to cover the emitter 36 and the detector 38, 40.

The segments 182 and 186 can be drawn into or between the two wall members 204, 230, as illustrated in FIGS. 10A and 10B. The segments 182 and 186 need not have a bottom panel that is coextensive with the bottom panel 232 of the fixed length segment 44, but can be separate wall members, including a first wall member 182a and a second wall member 182b and the fourth segment 186 can include a first wall member 186a and a second wall member 186b. It is understood, however, that connecting members 182c and 186c can optionally interconnect the respective wall members 182a, 182b and 186a and 186b.

Regardless of the specific configuration of the moveable segments 182, 186, the segment drive 200 and/or 206 can include a linkage 240 coupled to the second segment 182 and a second linkage 242 coupled to the fourth segment 186. The linkages 240, 242 can include hydraulic linkages, cables, fixed bar linkages, articulated bar linkages, or other appropriate linkages. According to an appropriate configuration the drive 200 and/or 206 can operate the linkages 240, 242 to move the second segment 182 and the fourth segment 186 relative to the fixed length segment 44 to move the segments 182, 186 between the "C" shaped configuration rotor 42 the "O" shaped configuration rotor 42'. Appropriate clearances can be provided between the segments 182, 186 and the fixed length segment 44 and the detectors 38, 40 of the imaging system 16. The segments 182, 186 can move on selected rails or track within the fixed length segment 44 to change between the "C" shaped configuration rotor 42 the "O" shaped configuration rotor 42'.

A lock device may also be provided to lock any of the moveable segments 180, 182, 184, and 186 relative to one another and/or the fixed length segment 44. The lock device may include a moveable pin or member that moves to engage at least two of the moveable segments 180, 182, 184, 186 and/or the fixed length segment 44. The lock device may also include locking or fixing the selected drives 100, 200, and/or 206. The lock device, however, holds the various segments in the selected configurations.

Accordingly, the imaging system 16 that may include the rotor 42, 42' may have the fixed length segment 44 and the movable segments 180, 182, 184, 186. The moveable segments 180, 182, 184, 186 can be moved relative to the fixed length segment 44 of to change the form of the imaging system between the C" shaped configuration rotor 42 the "O" shaped configuration rotor 42'. It is further understood that the first segment and the third segment 180, 184 can also move relative to the fixed length segment 44 of the gantry 42 in a manner similar to that illustrated and described as relative to the second and fourth segments 182, 186. The computer 32 may also be used to operate movement of the segments 180, 182, 184, 186 to reconfigure the transformable imaging system 16 from the "C" shaped configuration rotor 42 the "O" shaped configuration rotor 42', and vice versa. Also, the moveable segments may be provided in any appropriate number.

As illustrated in FIGS. 7-9, in various embodiments, the moveable segments 180, 182, 184, 186 may move from two ends of the fixed length portion 44. In the illustrated embodiment, opposing segments such as 184 and 186 move towards one another to complete the "O" shaped rotor 42'. It is understood, however, that various embodiments may differ from the specific example illustrated, but may incorporate portions of the specific embodiment illustrated in FIGS. 7-9.

In various embodiments, moveable segments, such as all of the moveable segments may extend from only one end (also referred to as a "top" or a "bottom") of the fixed length rotor segment 44. For example, rather than the moveable segments 184 and 186 moving towards one another, all of the moveable segments may collapse to one end of the fixed length segment 44 to form the "C" shaped rotor 42, such as near a bottom near the spindle 146, and then move out and towards a top of the fixed length segment 44. Upon reaching the top the moveable segments would then form the "O" shaped rotor 42'. The moveable segments may be stacked vertically relative to one another prior to moving to change the shape of the rotor. Further, the segments may telescope out to change the shape of the rotor.

In various embodiments, the number of moveable segments may be any appropriate selected number. For example, one, two, three, five, or more moveable segments may be provided. The arc length of each moveable segment may be selected, therefore, to configure the gantry from the "C" shaped rotor 42 to the "O" shaped rotor 42'. Thus, two moveable segments may include one moveable segment that moves from the bottom and another that moves from the top of fixed length portion 44 to meet to form the "O" shaped rotor 42'. Further, a single moveable segment may move from one end of the fixed length portion 44 to contact the other end to form the "O" shaped rotor 42'.

Figure 11:
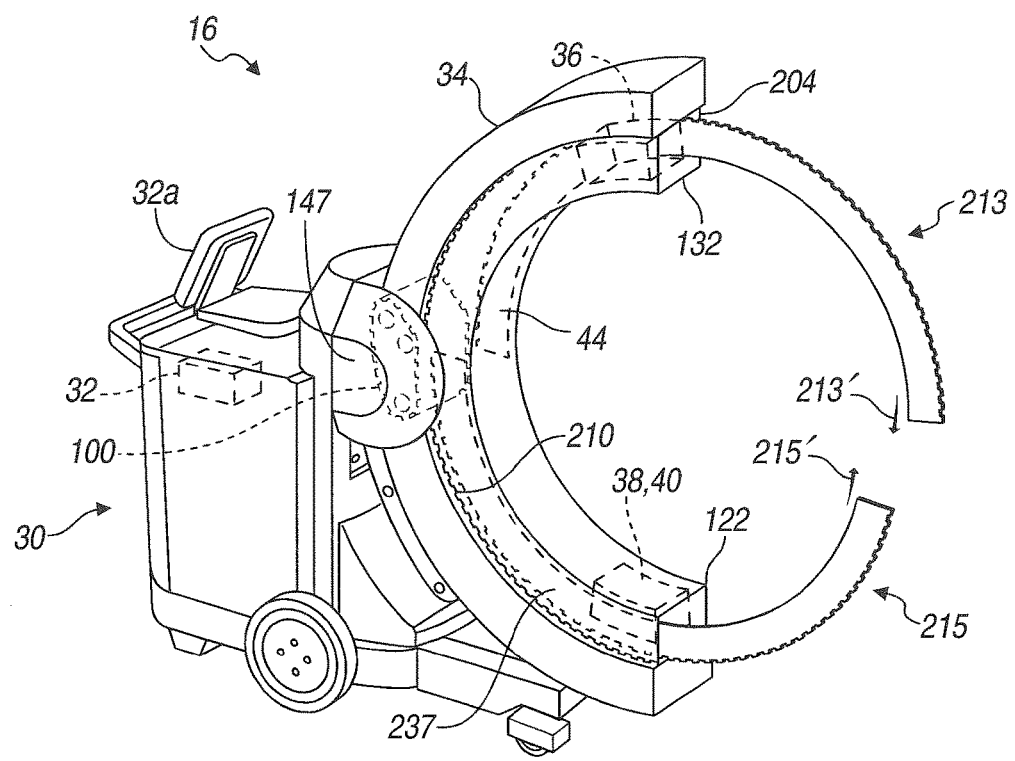
FIG. 11 is a perspective view of an imaging system, according to various embodiments.

In various embodiments, as illustrated in FIG. 11, the imaging system 16 may include a two portion moveable segment, having a first portion 213 and a second portion 215. The first portion 213 may extend from a first end 217 of the fixed length segment 44. The second portion 215 may extend from a second end 219 of the fixed length segment 44. Each portion 213, 215 moves in the direction of the respective arrows 213' and 215' towards the opposing ends 217, 219 of the fixed length segment 44. It is understood, however, that both of the portions 213, 215 may move in the same direction from one of the ends 217 or 219 towards the other 217 or 219 rather than the two portions 213, 215 moving from opposing ends of the fixed segment 44. The movement of the first and second portions 213, 215 may operate in a manner similar to movement of the moveable segments discussed above. Further, movement of the first and second portions 213, 215 causes the "C" shaped rotor 42 to be transformed to the "O" shaped rotor 42'.

Each of the first and second portions 213, 215 includes an arc length great enough to complete the "O" shaped rotor 42'. Each of the first and second portions 213, 215, however, only forms one side or surface of the "O" shaped rotor 42'. For orientation only, for example, the first portion 213 forms the left side and the second portion 215 forms the right side. In other words, each of the portions 213, 215 are near or adjacent to one of the exterior sidewalls 204, 230 of the fixed length segment 44.

Each of the first and second portions 213, 215 may include track portions to complete the track for movement of the source 36 and the detector(s) 38, 40 or the track to move the "O" shaped rotor 42' relative to the gantry 34. In various embodiments, the fixed length segment 44 may form about 180 degrees of a circle and each of the first and second portions 213, 215 may each form about 180 degrees of a circle. Thus, movement of the first and second portions 213, 215 may form the "O" shaped rotor 42'. It is also understood that each of the portions 213, 215 may be formed of multiple members to form the first and second portions 213, 215.

Telescoping Segmented Gantry

In various embodiments, including those discussed above, the imaging system 16 can be provided as specifically illustrated, including in FIGS. 1 and 2, or may be altered or replaced with various features including those discussed further herein. With initial reference to FIGS. 12A-12E, an imaging system 316 is illustrated. The imaging system 316 can included portions and features that are substantially identical to the imaging system 16 discussed above. For example, the imaging system 316 can include the cart 30, the imaging computer 32, the base 112, the connection or arm 147, and at least one drive motor or mechanism 100. The imaging system 316 may also be augmented to include portions of the imaging system 16, as discussed above, as understood by one skilled in the art. Nevertheless, the imaging system 316 can include certain features as discussed further herein.

The imaging system 316 may include a gantry 334 that has an unchanging gantry portion or segment 334a. The unchanging portion 334a may also be referred to as a static or non-adjustable portion. In various embodiments, the static portion 334a has a fixed dimension (e.g. an arc length) and other segments may move relative to the static segment 334a. For example, the unchanging gantry portion 334a can form or define an arc that has a center, such as an isocenter of an imaging system, which is less than 180°. The unchanging portion 334a forms at least a part of an arc between a first end 334a' and a second end 334a". Further, the unchanging portion 334a may have a height 334x at an upper most or highest point 334y' of the unchanging portion 334a above a surface 334y, such as a floor on which the imaging system 316 is placed, that is about five feet (about 1.5 meters) or less, including about five feet six inches (about 1.6 meters) in height. It is understood by one skilled in the art that the height of the unchanging portion 334a may be selected for various purposes, such as to allow a user of a selected height to see over the unchanging portion 334a.

According to various embodiments therefore, the imaging system may define a maximum dimension that is less than a selected amount. For example, the unchanging gantry portion 334a may further include a height or upper dimension that may be no higher or shorter than eye or sight line level of an average person that may move the imaging system 316. This may assist in ease of movement of the imaging system and viewing relative to the imaging system 316, especially when an operator moves the cart 30 of the imaging system 316. The gantry 334, having the unchanging gantry portion 334a, therefore, allows for a smaller dimension extending from a portion of the cart 30 opposite or away from the monitor 32a, where an operator may be positioned when moving the cart 30. Thus, the imaging system 316 allows for a selected clearance and efficient mobility.

The gantry 334 can include one or more outer wall segments, such as four outer wall segments 350, 352, 354, and 356 (see FIGS. 13 and 14) that form a cross-section with a volume inside of the wall segments 350, 352, 354, and 356. The cross-section may be a selected geometry. For example, as illustrated, the cross-section may include a rectangular cross-section.

The gantry 334, therefore, can define a space within the wall segments in which a portion can move, such as the emitter 36 and detectors such as the detectors 38 and 40. The cross-sectional area of the wall segments 350, 352, 354, and 356 can also house movable portions that allow the gantry 334 to change shape from the portion formed by the unchanging portion 334a to other shapes, including those discussed further herein and illustrated in FIGS. 12B-12E. As discussed further herein, the segments included or positioned within the volume defined by the wall segments 350, 352, 354, and 356 can be moved relative to the non-changing portion 334a of the gantry 334 to change a shape of the gantry 334 and/or an operation of the imaging system 316.

Further, positioned within the cross-sectional area defined by the wall segments 350, 352, 354, and 356 can be a rotor 342. The rotor 342 can be similar to the rotor 42, as discussed above. For example, the source 36 and the detectors 38-40 may be mounted to the rotor 342. The rotor 342 can move within the gantry 334 to allow for imaging of a subject, such as the patient 14.

It is understood, in various embodiments, the rotor 342 may be positioned or provided to be immobile for various operational reasons. For example, with reference to FIG. 12A, the imaging system 316 can be provided in a stowed or transportation configuration. In a transportation configuration, the gantry 334 is formed or has terminal extents or perimeters defined only by the non-changing portion 334a. The rotor 342 can be positioned within the non-changing gantry portion 334a. The rotor 342 may be formed of collapsible portions to allow the rotor 342 to be collapsed to fit within the non-changing gantry portion 334a. The rotor 342, as discussed above, may also include the source 36 and the detectors 38-40 associated therewith. Thus, the source 36 and the detectors 38-40 may be retracted or positioned within the non-changing gantry portion 334a. In the collapsed or transportation configuration, as specifically illustrated in FIG. 12A, the imaging system 316 can be efficiently moved and stored in a facility, such as a hospital. The small configuration or collapsed configuration may also allow for greater access to the patient 14 by the user 12.

Figure 12A:
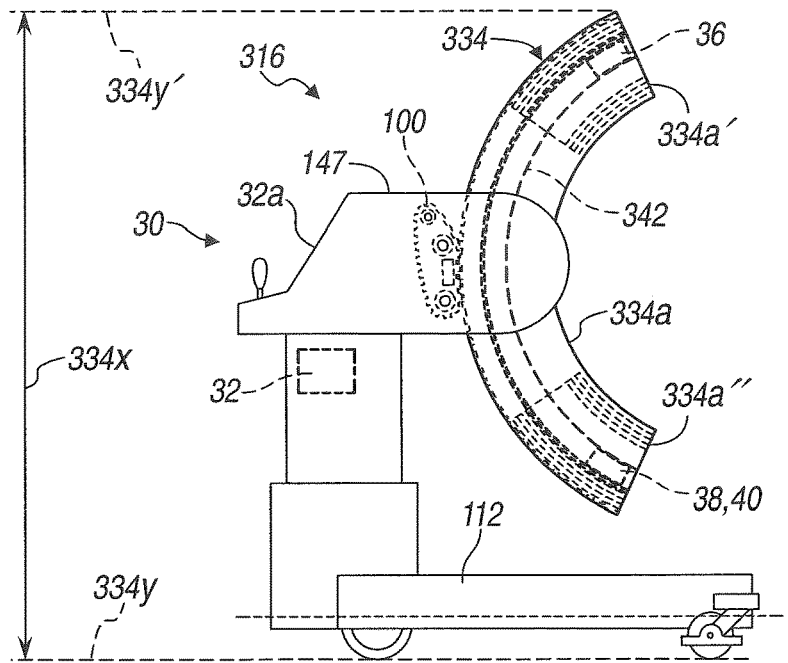
FIG. 12A is a side plan view of an imaging system, according to various embodiments, in a first configuration.
Figure 12B:
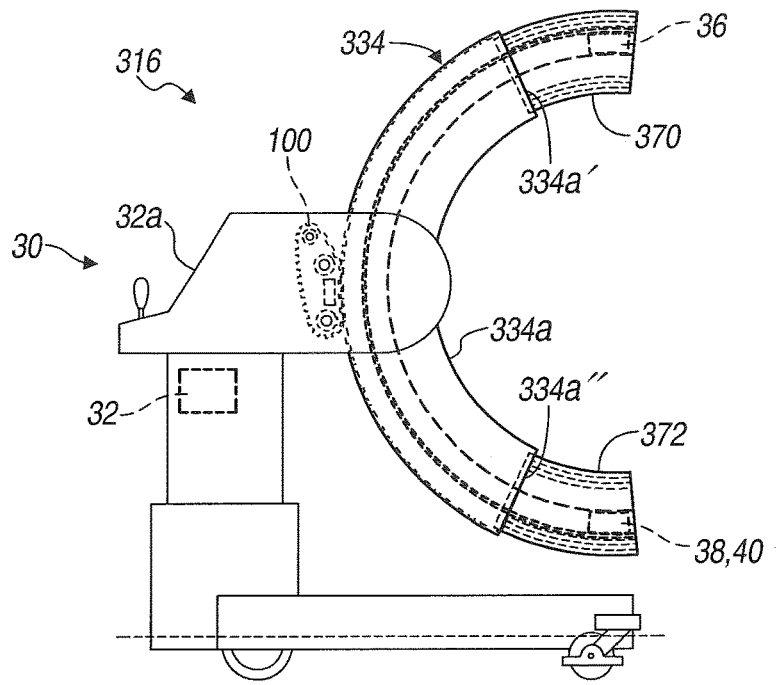
FIG. 12B is a side plan view of an imaging system, according to various embodiments, in a second configuration with segments extended.

With reference to FIG. 12B, the gantry 334 may be operated to change its configuration. The configuration of the imaging system 316, therefore, can be changed to allow operation of the imaging system 316 in various operational manners. In various embodiments, as discussed herein, one or more pieces of the gantry may move, one of more pieces of the rotor 342 may move, or combinations thereof to change the configuration of the imaging system 316. The configuration may be changed for difference purposes, such as operation of the imaging system in different and selectable manners and/or movement and storage of the imaging system 316.

Transformation or changing the configuration of the gantry is illustrated in FIGS. 12B-15. Discussion herein includes reference to FIGS. 12A-15 in addition to a specific segmental change as illustrated in FIGS. 12B-12E. As illustrated in FIG. 12B, a first movable portion 370 and a second movable portion 372 can extend (e.g. telescope) from the non-changing portion 334a of the gantry 334, is illustrated in FIG. 12B. In particular, the first and second movable portions 370-372 can extend from within the volume formed by the exterior wall segments 350-356. As discussed further herein, the first movable portions 370, 372 can each include an external wall portion, such as a wall section 380, 382, 384, and 386. Each of the wall segments 380, 382, 384, and 386 can form an internal volume, as also discussed further herein. Further, the wall segments 380, 382, 384, and 386 can form an external taper or have an angle relative to a longitudinal axis or a central axis formed through the internal volume of the movable portions 370-372.

Figure 13:
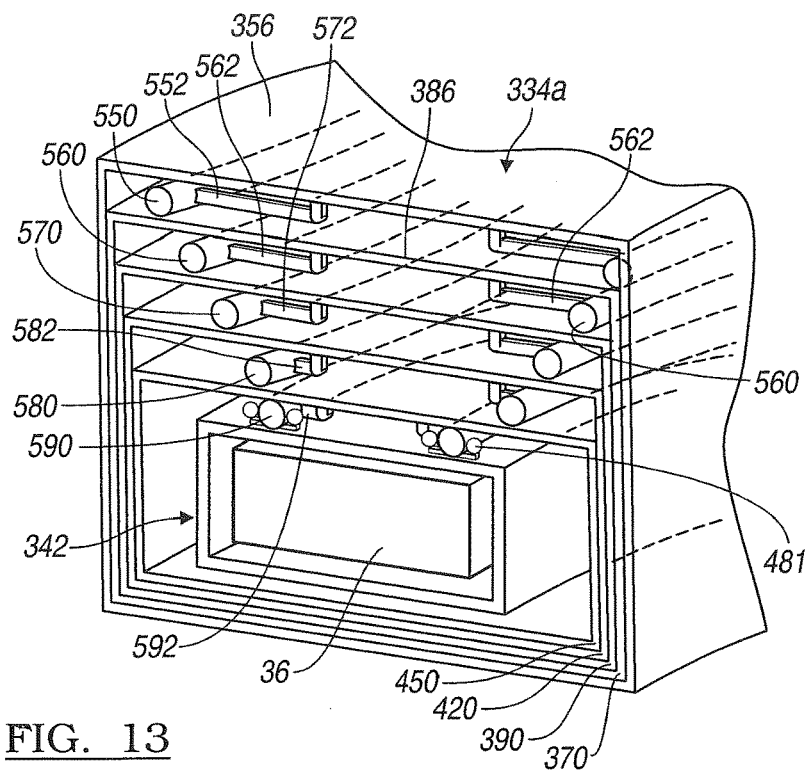
FIG. 13 is a detail view of an end of the imaging system of FIG. 12A with segments collapsed.

The angle of the walls or surface of the wall segments 380, 382, 384, and 386 of the segments 370-372 can cause the segments to engage the non-changing portion 334a. The external walls 380, 382, 384, and 386 engage internal surfaces of the wall segments 350-356 to assist in engaging or holding the first movable portions 370-372 relative to the non-changing gantry portion 334a. The engagement may occur as the movable portions 370 and 372 move out from the non-changing gantry portion 334a. In moving out, the taper of the external walls 380, 382, 384, and 386 move closer to and then engage the internal surfaces of the walls of the non-changing gantry portion 334a, as illustrated in FIGS. 11B and 13. When engaged, the movable portions 370 and 372 may be at least partially supported and fixed by the engagement. As discussed herein, further movable portions may be similarly held.

Figure 12C:
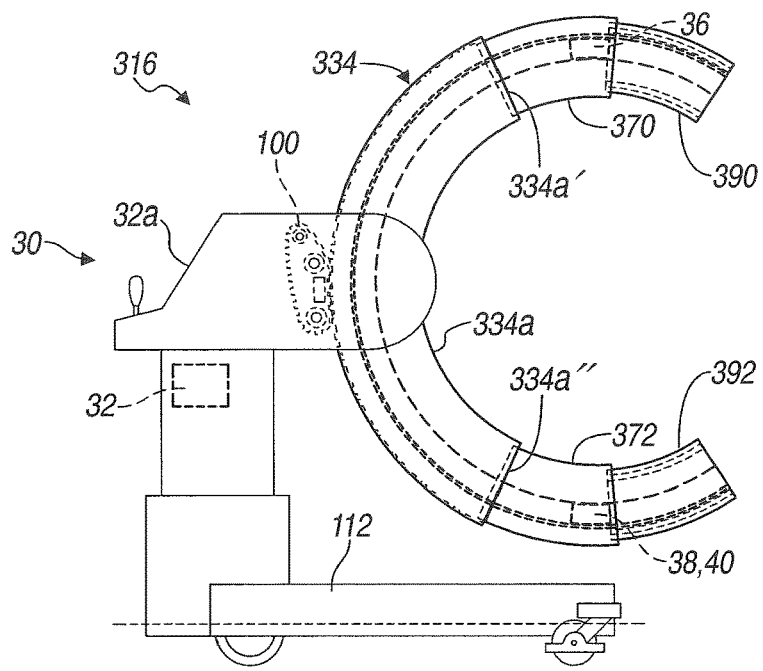
FIG. 12C is a side plan view of an imaging system, according to various embodiments, in a third configuration with segments extended.

With continuing reference to FIG. 12B and additional reference to FIG. 12C, a third movable portion 390 and a fourth movable portion 392 can move relative to the first and second movable portions 370-372, respectively. Again, each of the third and fourth movable portions 390, 392 include wall segments, such as wall segments 400, 402, 404, and 406. Again, the wall segments 400, 402, 404, and 406 can taper or form an angle relative to an internal surface of the respective wall segments 380-386 of the first movable portions 370-372. The taper or angle can assist in engaging or holding respective third and fourth movable portions 390-392 relative to the first and second movable portions 370-372.

Figure 12D:
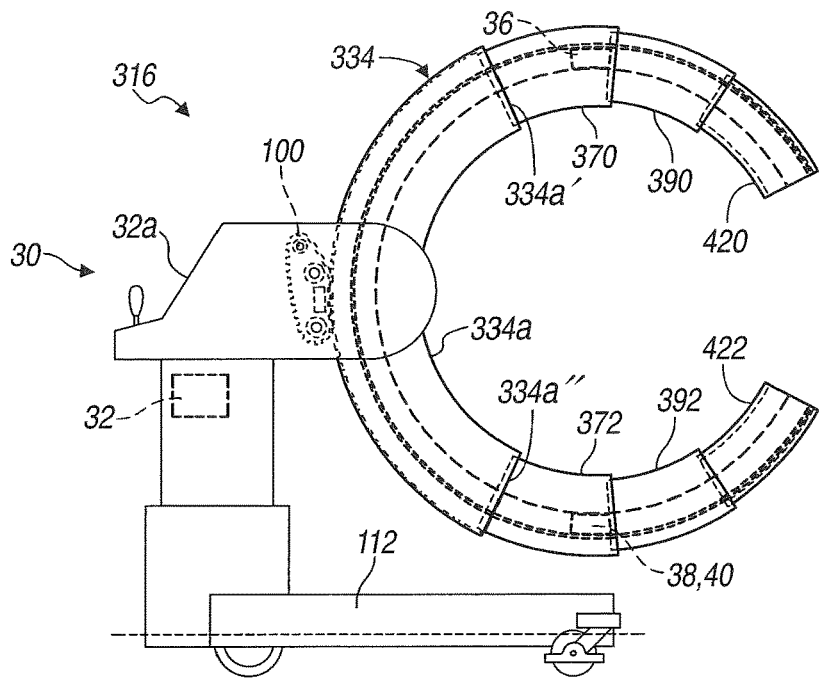
FIG. 12D is a side plan view of an imaging system, according to various embodiments, in a fourth configuration with segments extended.

Turning reference to FIG. 12D, a fifth movable portion 420 and a sixth movable portion 422 can move relative to the third and fourth movable portions 390, 392, respectively. Again, each of the fifth and sixth movable portions 420, 422 can include external wall segments, such as external wall segments 430, 432, 434, and 436. Each of the wall segments 430, 432, 434, and 436 can engage or contact an internal surface of wall segments 400, 402, 404, and 406 in the extended configuration, as discussed above. Each respective movable portion can move relative to and engage or assist in holding the next extending movable portions.

Figure 12E:
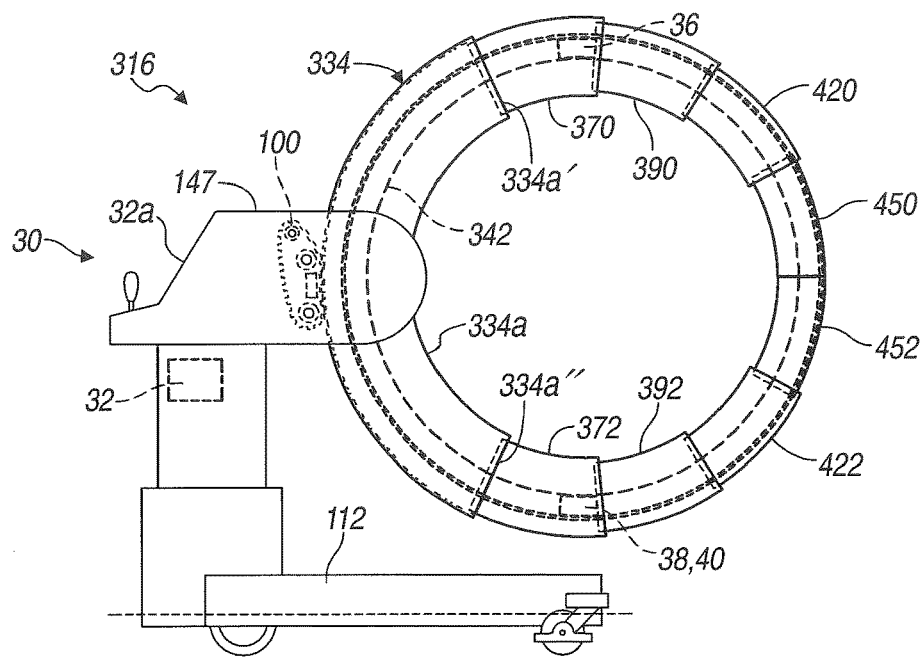
FIG. 12E is a side plan view of an imaging system, according to various embodiments, in a fifth configuration with segments extended.

Finally, with reference to FIG. 12E, a seventh movable portion 450 and an eighth movable portion 452 can extend from the respective fifth and sixth movable portions 420, 422. Again, the seventh and eighth movable portions 450-452 can include external wall segments, such as four wall segments 460, 462, 464, and 466. The wall segments 460, 462, 464, and 466 can again include an external taper or angle relative to an internal surface of the wall segments 430, 432, 434, and 436 to assist in engaging or holding the seventh and eighth movable portions 450, 452 relative to the fifth and sixth movable portions 420, 422 in a manner similar to that discussed above.

Illustrated in FIGS. 12A-12E and discussed above is an example of various embodiments wherein the moveable portions extend from both ends 334a', 334a" of the non-changing gantry portion 334a. It is understood, however, that in various embodiments that all of the moveable segments may extend from only one of the ends 334a' or 334a". In various further embodiments, an unequal number of the moveable segments may move from either one of the ends 334a' or 334a" (for example five segments extend from the end 334a' and three segments extend from the end 334a"). Regardless, the gantry 334 may be transformed or reconfigured to various shapes including a "C" shape and an "O" shape for operation and/or transport of the imaging system 316.

It is further understood that the imaging system 316 by including the plurality of moveable segments may allow the imaging system 316 to achieve various shapes between a fully open "C" shape and the "O" shape. For example, the "C" shape may be provided to have an arc length only equal to the unchanging portion 334a. The "C" shape may then be changed to have an arc length of less than one moveable segment in addition to the unchanging portion 334a. Additional length may be added in small portions without completing the "O" shape and up to the "O" shape. Thus, the multiple moveable segments allow for a large range of user selectability of size for the gantry, including any arc length between the fully open "C" shape (with the moveable segments retracted completely) to the "O" shape.

With reference to FIGS. 12 and 13, the non-changing gantry portion 334a and the respective movable gantry portions 370, 390, 420, and 450 are illustrated. It is understood that the movable portions 372, 392, 422, and 452 may include a similar geometry and configuration and are therefore not repeated, but are understood to include features as discussed further herein. As discussed above, the non-changing gantry portion 334a includes the wall segments 350-356, and each wall segment 350-356 can include internal surfaces thereof that engage external surfaces of the wall segments 380-382 of the first movable portion 370. Further, the third movable portion 390 includes the external wall segments 400-406 that can include a geometry and configuration to engage internal surfaces of the wall segments 380-386. The fifth movable portion 420 includes the wall segments 430-436 that may have external surfaces to engage internal surfaces of the wall segment 400-406 of the third movable portion 390. Finally, the seventh movable portion 450 includes the external wall segments 460-466 that may have surfaces to engage internal surfaces of the wall segments 430-436 of the fifth movable portion 420.

The various wall segments and surfaces allow the movable portions 370, 390, 420, 450 to move a selected amount relative to each other and the non-changing gantry portion 334a. Further, the various wall segments and surfaces may allow the movable portions 370, 390, 420, 450 to move to selected positions and be held or fixed relative to each other and the non-changing portion 334a. For example, as each of the movable portions 370, 390, 420, 450 are moved relative to the non-moving portion 334a, the wall segments allow the respective movable portions 370, 390, 420, 450 to move and engage in a fixed selected position relative to the non-changing portion 334a and/or the other movable portions. This allows the various configurations of the imaging system 316 to be achieved. Specific configurations of the internal wall surfaces and external wall surfaces can be selected to achieve various rigidities and may be based on material selection of the gantry 334, therefore, exemplary embodiments are discussed herein for illustration purposes only.

With continuing reference to FIG. 13, the gantry 334 including the non-changing portion 334a and the various movable portions 370, 390, 420, 450, are illustrated in extended and semi-extended configurations. The movable portions move relative to the non-changing portion 334a to allow the gantry 334 to change shape from the shape illustrated in FIG. 12A to a substantially "O"-shape or annular shape as illustrated in FIG. 12E. The various movable portions 370, 390, 420, 450 can be moved relative to the non-changing portion 334a according to various mechanisms, including linkages, individually mounted servo motors, and the like.

For instance, a linkage system can be interconnected with a single motor, such as the motor 100, to sequentially move and selectively move each of the movable portions 370, 390, 420, 450 relative to the non-changing portion 334a. Alternatively, or in addition to the linkage, a servo motor or selected motor can be interconnected with each of the movable portions 370, 390, 420, 450 that can be individually operated to move the selected movable portion relative to another of the movable portions 370, 390, 420, 450 and/or the non-changing portion 334a. Either or both of these systems may drive wheels 481. The wheels 481 may also only provide a guide or bearing for the movement of the movable portions 370, 390, 420, 450. In this manner, the gantry 334 can be changed between selected configurations from the fully opened or collapsed configuration illustrated in FIG. 12A to a closed or annular configuration as illustrated in FIG. 12E.

Figure 14:
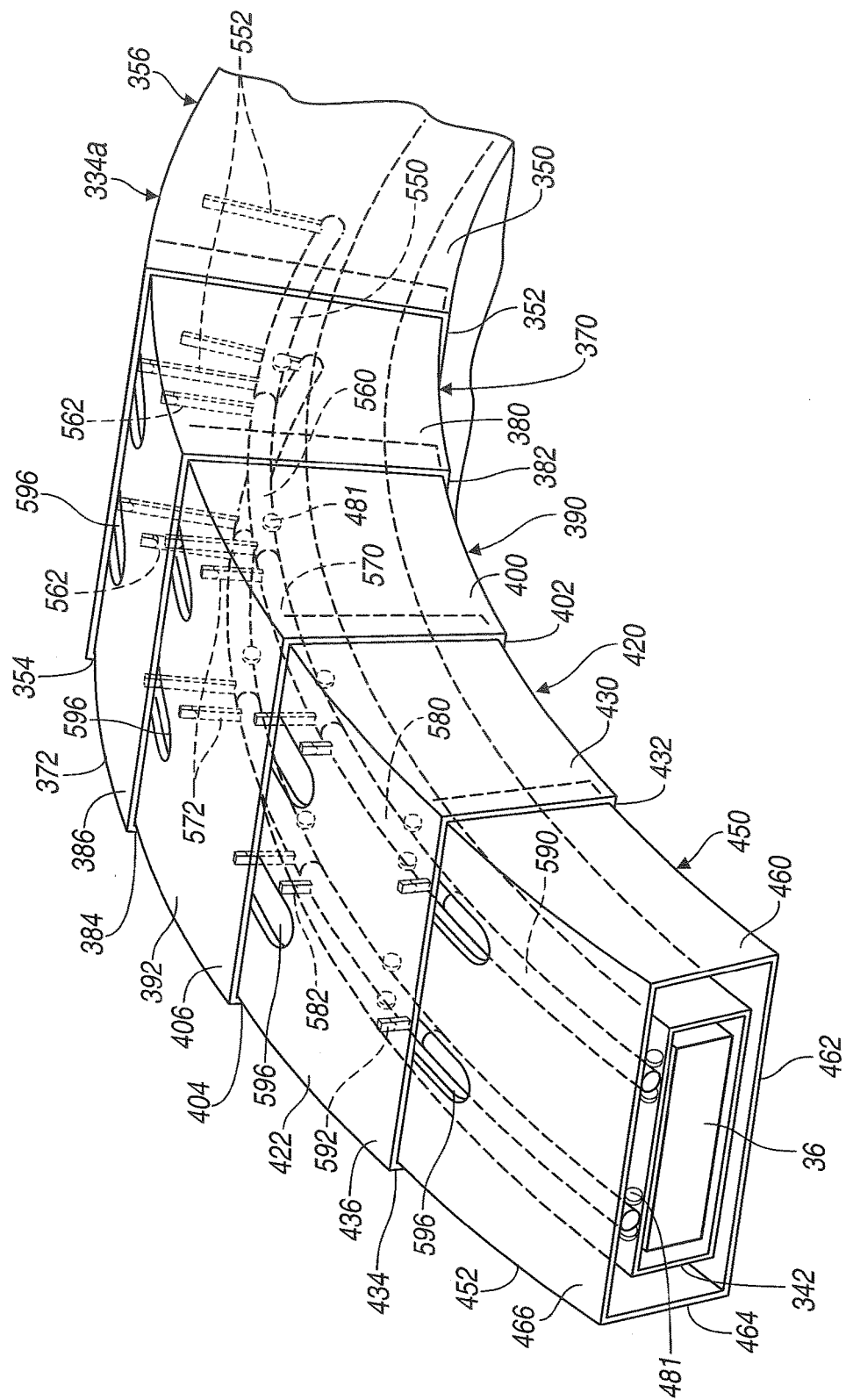
FIG. 14 is a detail view of an end of the imaging system of FIG. 12D with segments extended.
Figure 15:
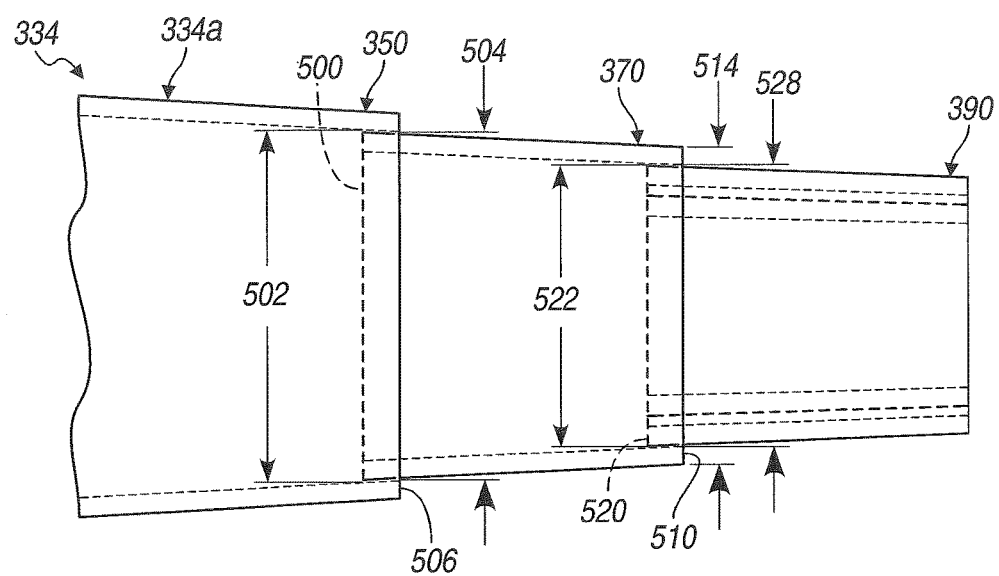
FIG. 15 is a top plan view of the imaging system of FIG. 12D with segments extended.

With additional reference to FIG. 14, an end of the non-changing portion 334a and two movable portions 370 and 390 are illustrated. The movable portions can include a shape or geometry mentioned above and illustrated in greater detail here. A first terminal end of the first movable portion 370 includes a first terminal end 500 that includes at least one dimension, such as an external width dimension 502. The external dimension 502 may be greater than an internal terminal end dimension 504 at a second terminal end 506 of the non-changing portion 334a. In this way, as the movable portion 370 moves out of the non-changing gantry portion 334a, the wall segments 380-386 can engage, such as interferingly engage the internal surface of the non-changing gantry portion 334a. A third terminal end 510 of the first movable portion 370 may include an external dimension 514 that is less than the external dimension 502 of the non-changing portion. In this way, the first movable portion 370 tapers from the first terminal end 500 to the third terminal end 510.

An opening, such as a cross-sectional opening defined by the wall segments 350-356 of the non-changing gantry portion 334a include the internal dimension 504 that is greater than the dimension 514 of the third terminal end 510, but it less than the external dimension 502 of the first terminal end 500. Accordingly, as the second movable portion 370 moves out of the non-changing gantry portion 334a, a physical interference occurs between the movable portion 370 and the non-changing gantry portion 334a. This physical interference, along with any other selected locking mechanisms, such as a pin and wedge and the like, hold the movable portion 370 relative to the non-changing gantry portion 334a in a selected shape or configuration.

It is understood that the other movable portions can also include a similar configuration relative to the portions to which they move. For example, the third movable portions may include a fourth terminal end 520 that has an external dimension 522 that is greater than an internal dimension 528 of the third terminal end 510. Thus, the third movable portion 390 may move and physically engage the second movable portion 370.

Thus, a terminal end may include an external cross-sectional area, such as defined at least in part by the dimensions noted above, that is greater than an internal cross-sectional area at a second terminal end. The greater cross-sectional area being smaller than an opening through which the movable portion moves. Thus, a physical interference and connection can be formed between the various moving portions to form the gantry 334 in a selected shape that may be changed between the substantially open shape illustrated in FIG. 12A and the O shape illustrated in FIG. 12E.

Returning reference specifically to FIGS. 13 and 14, as discussed above, the emitter 36 and selected detectors 38, 40 can be positioned on the rotor 342 to rotate within the gantry 334. The rotor 342 may move on a track, such as a track formed by one or more track members. The track members can include a first or first pair of track members 550 movably connected by a linkage or pair of linkages 552 to the fourth wall portion 356 of the non-changing gantry portion 334a. The first rail or track member 550 can extend the entire arcuate dimension of the non-changing portion 334a of the gantry 334. The track members 550 allow for the rotor 342 to engage relative to the gantry 334 and allow movement of the rotor 342 relative to the gantry 334.

The track can also include rail members, as discussed further herein, that are interconnected with the various movable portions 370-452. For example, one or a pair or second number of track members 560 can be movably connected with the first movable portion 370 by one or more linkages 562. A third track member or members 570 can be movably interconnected with the third movable portion 390 by one or more linkages 572. Fourth track member or members 580 may be movably interconnected with the fifth movable portion 420 with movable linkages of 582. Also, fifth track member or members 590 can be interconnected with the seventh movable portion 450 with linkages 592. The linkages 592 may not need to be movable relative to the movable portion 450. The track members 590 may be fixably connected to the seventh movable portion 450 as the diameter formed by the fifth track members 590 relative to the seventh movable portion 450 may define the circumference of the completed track for movement of the rotor 342. It is understood, however, that the fifth track members 590 may be also movably mounted relative to the seventh movable portion 450. Moreover, it is understood that the opposing movable portions 372-452 may also include track members similar to the counterpart track members 550-590, discussed above, but are not repeated here for clarity of the current discussion.

According to various embodiments, as the movable portions, for example, the first movable portion 370, moves from the non-changing gantry portion 334a, the first track member 550 can be moved either alone or in combination with the second track portion 560 to form a complete track extending from the non-changing gantry portion 334a. Similarly, as each of the other movable portions 390, 420, 450 move, the various track portions can move to align the track members to form a track for the rotor 342 to ride along.

To assist in providing clearance for the track members to move relative to each other and the various movable portions 370-450, the top walls or a portion of the top wall may include one or more grooves 596 to allow at least an end portion of the respective track members to move through the respective top walls of the movable portions 370-450. Thus, the track members may move from a collapsed or retracted position, as illustrated in FIG. 13, into aligned positions with the respective track members. It is further understood that the track members can move any appropriate amount and the amount illustrated in the drawings is simply for the current discussion and illustration.

Further, when the movable portions are held within the other respective movable portions and/or the non-changing gantry portion 334a, the track members 520-560 can be retracted or withdrawn into space between respective wall segments of the gantry portions. As illustrated in FIG. 13, the track member 550 is between the wall segment 356 of the non-changing gantry portion 334a and the top wall segment 386 of the second movable portion 370. Similarly, the other track members can be retracted into a space provided between each of the respective gantry portions, as exemplarily illustrated in FIG. 13. The track members may be moved into the track forming position as illustrated in FIG. 14.

The track portions, including the tracked portions 550, 560, 570, 580, 590, can be moved from the retracted position to the extended position to form the track for movement of the rotor 342 using various mechanisms such as individual servo motors for each of the tracked portions, connected linkages to a drive (e.g. the drive 100), or other appropriate movement mechanisms. For example, individual servo motors or linkages can be included in each of the movable portions 370-452 to move the track members to be deployed position once the movable portion is in a selected position, such as deployed to an operating position. Further, the movement of the track members can be provided to move gradually such that as the movable portion is moving to the deployed or operating position, the track member can also be moving simultaneously. In this way, the track member can reach the deployed position and the movable portion can reach the deployed position substantially simultaneously.

Moveable Source and Detector

An imaging system for acquiring images of a patient, including those discussed above is disclosed according to various embodiments. Alternatively, or in addition to the specific examples illustrated and discussed above, an imaging system 700, according to various embodiments, is illustrated with initial reference to FIGS. 16A-16E. The imaging system 700 can include portions that are similar to the portions discussed above and will not be described in detail here. For example, the imaging system 700 may include the cart 30 which may be movable, such as being pushed by an operator manually or powered with a motor, via wheels 31 or other appropriate mobility devices. The imaging system 700 may further include a display device (e.g. a monitor) 32a which may be used to monitor operation of the imaging system 700 and/or view images acquired with the imaging system 700. The imaging system 700 may further include the imaging computer 32 which may process images on the imaging system 700 and/or transmit image data to other processing systems. Further, the motor 100 can be used to move various portions of the imaging system 700, such as with a control input (e.g. a stick) 702. Portions of the imaging system 700 that may be moved include a rotor 710.

In various embodiments, the imaging system 700 may be an x-ray or fluoroscopy imaging system. In these embodiments, the imaging system 700 will include a source, which is operable to emit x-rays, and one or more detectors such as the first detector 38 and the second detector 40. As initially illustrated in FIG. 16A, the source 36 and the detectors 38, 40 can be positioned at a selected location relative to the rotor 710. The source 36 may move with and/or independently of the detectors 38, 40. Further, each of the detectors may move independently of each other and/or the source 36.

The rotor 710 can be moved relative to the cart 30, such as with a connection or arm 147 to a base portion of the cart 30, as discussed above. The motor 100 may be incorporated into the connection 147 and may connect or engage the rotor 710, with one or more teeth 712 formed or provided on an exterior surface of the rotor 710. The rotor 710 can include a fixed or unchanging segment 716 on which the teeth 712 are formed. The unchanging fixed rotor portion 716 can extend along an arc from a first end 718 to a second end 720. For the unchanging portion 716, the length of the arc is not changeable by a user, as discussed above. Although the entire rotor 710 may be reshaped, according to various embodiments (e.g. telescoping segments), the unchanging portion or segment 716 does not have a length, i.e. arc length, which is changeable.

It is understood, however, that the rotor 710 need not move relative to the cart 30. As discussed herein, the source 36 and the detectors 38, 40 may move relative the cart 30 and to each other. Thus, the rotor 710 need not move relative to the cart to alter a position of the source 36 relative to one or more of the detectors 38, 40. As discussed herein, the rotor 710 may include a moveable portion that may allow the imaging system to form a fully annular track system. Thus, the imaging system 700 need not have a moveable rotor and only the source 36 and the detectors 38, 40 may move. It is understood, however, that both the rotor 710 and the source 36 and detectors 38, 40 may move and all may move independent of the others.

The patient 14 may be positioned near the isocenter 110 of the rotor 710, in a manner similar to that discussed above to the other imaging exemplary embodiments. The patient 14 can then be imaged with the imaging system 700, in a manner as generally understood by one skilled in the art, by emitting x-rays from the source 36 to be detected by selected one or more of the detectors 38, 40. The imaging system 700 may hold the source 36 and the detectors 38, 40 relative to one another during the imaging.

The rotor 710 may be interconnected with the connection 147 directly and/or through linkages. The rotor 710 also may engage the motor 100. For example, a track or engaging portion can movably couple the rotor 710, such as the unchanging rotor portion 716 directly to the connection 147. It is understood, however, a gantry 726 (illustrated in phantom), may also be provided to extend from the connection 147. The gantry 726 may be similar to the gantry 34, discussed above, and may support the rotor 710 during movement. It is understood, however, that the gantry 726 is not required for operation of the imaging system 700.

Figure 16B:
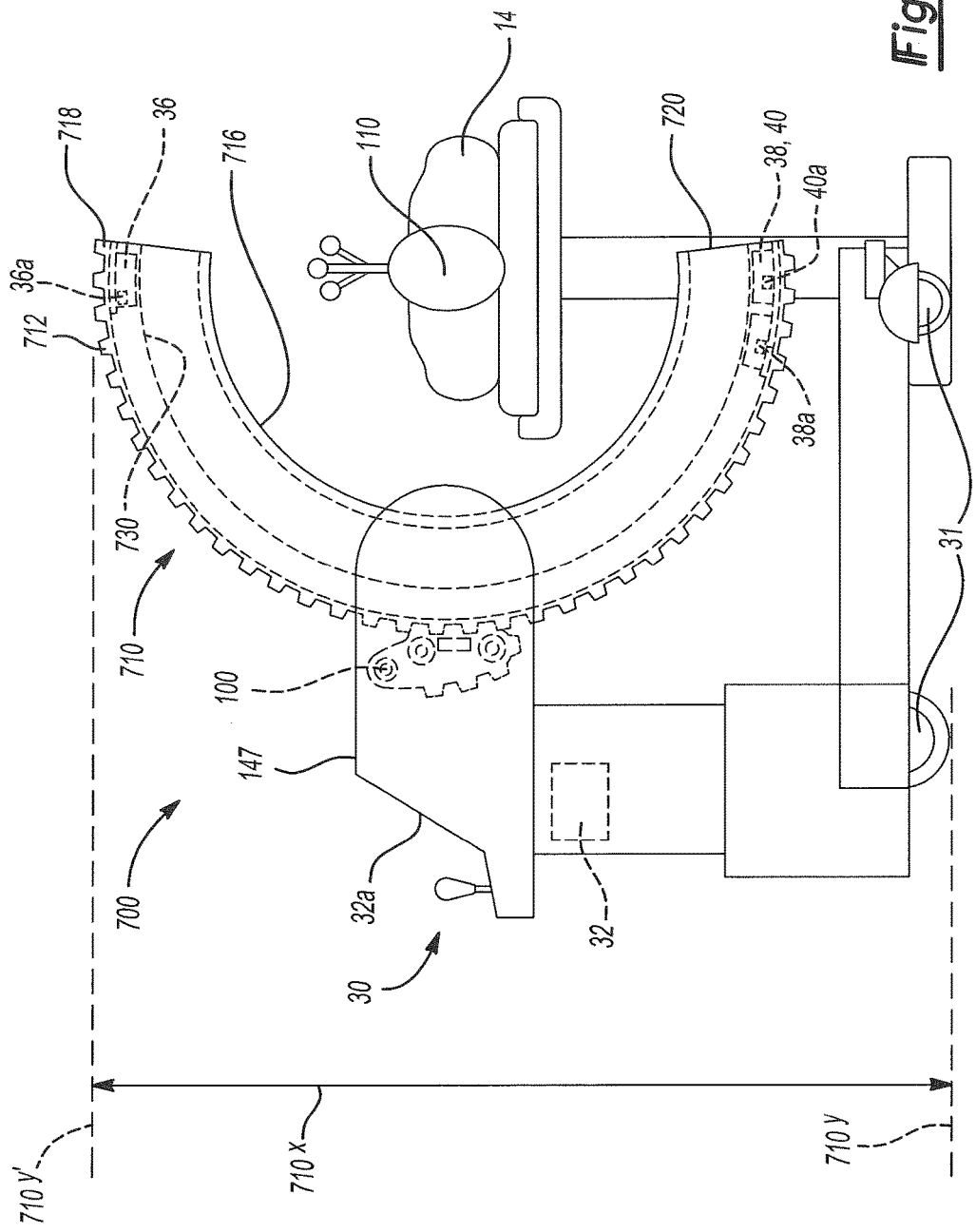
FIG. 16B is an environmental view of an imaging system, according to various embodiments, with a source and detector located away each other.
Figure 16C:
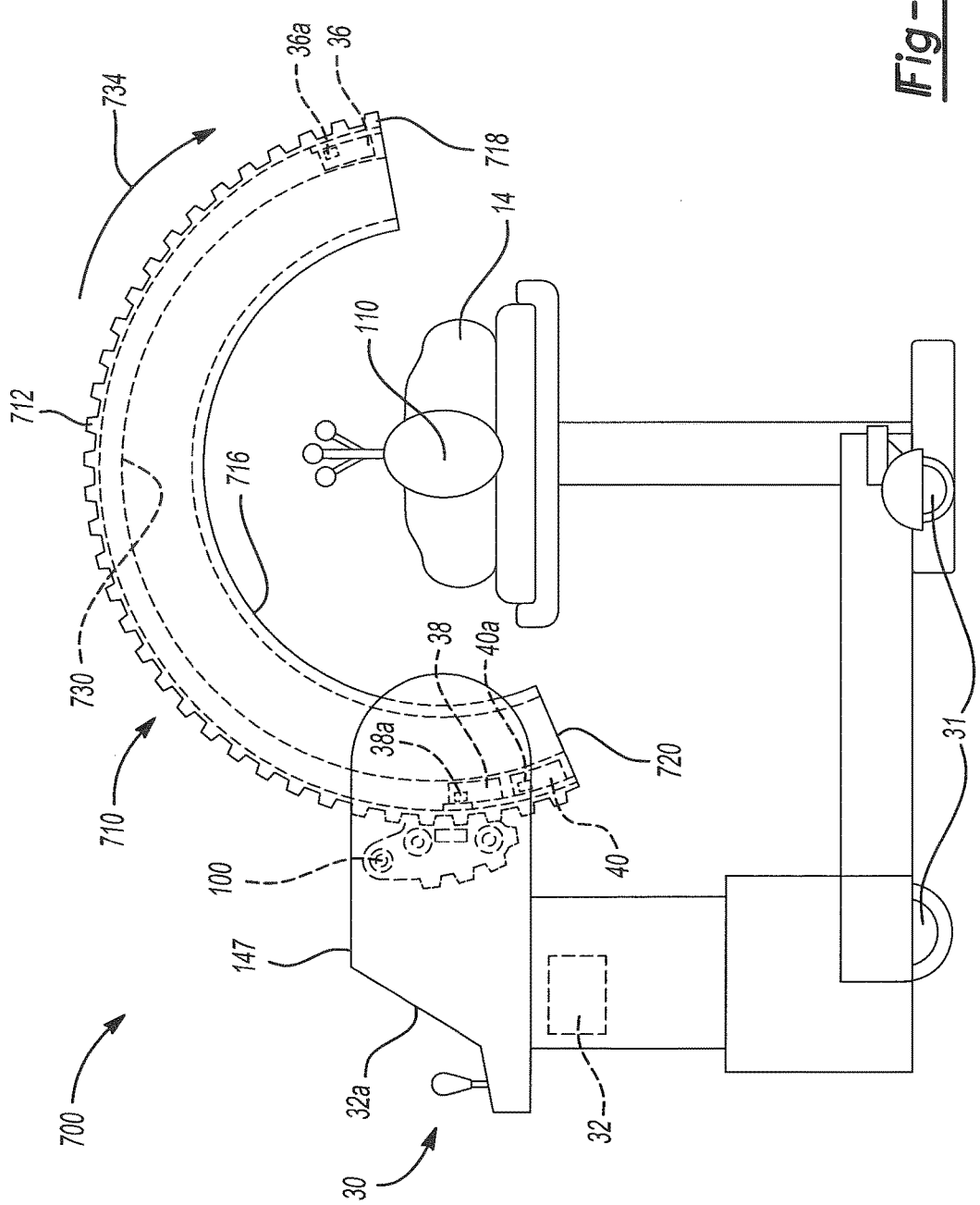
FIG. 16C is an environmental view of an imaging system, according to various embodiments, with a source and detector located away each other and a gantry in an alternate location.
Figure 16E:
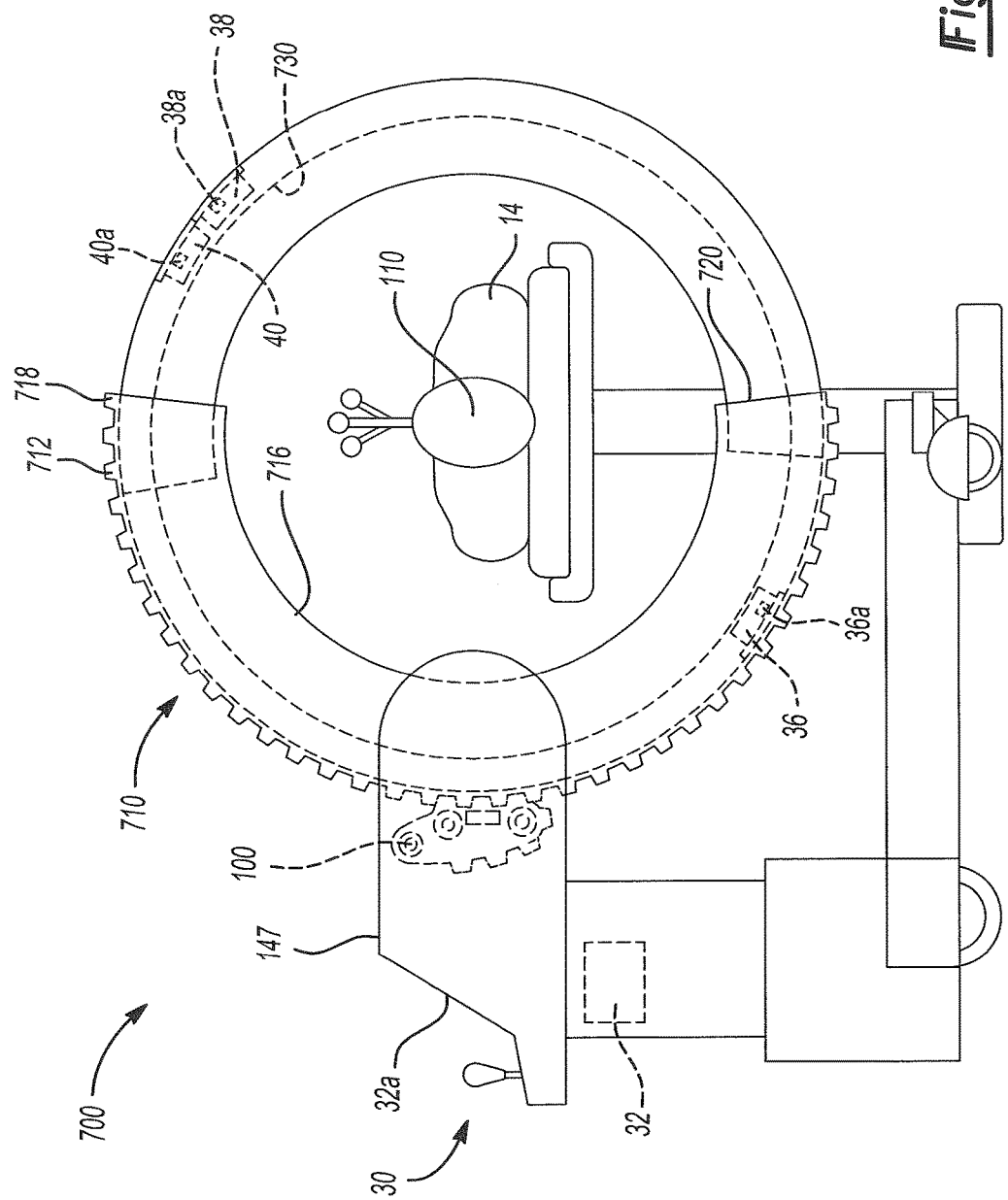
FIG. 16E is an environmental view of an imaging system, according to various embodiments, with a source and detector located away each other and a moveable portion of the gantry extended in an "O"-shape.

The imaging system 700 can be operated in a manner to collect image data of the patient 14 in a manner similar to that discussed above. The rotor 710, however, can be manipulated to be configured between a generally "C"-shaped configuration, as illustrated in FIG. 16B, and an "O"-shaped configuration as illustrated in FIG. 16E. A moveable segment 750 of the rotor 710 may move relative to the unchanging segment 716, as discussed herein, to change the shape of the rotor 710

The rotor 710 can house or contain the source 36 and the detectors 38, 40. Again, it is understood, that only a single detector may be provided or more than two detectors may be provided. Nevertheless, both the source 36 and the detectors 38, 40 can move within and relative to the rotor 710, including the non-changing portion or fixed segment 716. Further, as discussed above, the rotor 710 may also move relative with the cart 30 independently of the movement of the source 36 and the detectors 38, 40.

According to various embodiments, a track including a rail member 730 may be positioned within the non-changing segment 716. Each of the source 36 and the detectors 38, 40 can then be moved along the rail 730 to selected positions to acquire image data of the patient 14. As illustrated in FIG. 16A, the source 36 may be positioned near the detectors 38, 40, such as near the arm 147. As illustrated in FIG. 16B, the source 36 can also be positioned substantially opposite the detectors 38, 40 to acquire an image of the patient 14. The source 36 can move from the position as illustrated in FIG. 16A to the position as illustrated in FIG. 16B and the detectors 38, 40 can also move from the position as illustrated in FIG. 16A to the position as illustrated in FIG. 16B. When positions are substantially opposite one another, the imaging system 700 can acquire image data of the patient 14 in a selected manner, such as collecting x-ray projections through the patient 14.

It is understood that the non-changing segment 716 can be moved relative to the connection 147 to acquire image data at difference projections (i.e. angles of the detectors 38, 40) relative to the patient 14. For example, the non-changing portion of the rotor 716 can generally move in the direction of arrow 734, as illustrated in FIG. 16C, to a position about 90° from the position as illustrated in FIG. 16B. It is further understood that the non-changing portion 716 can generally move in the direction of arrow 736 to a position that is substantially 180° from that illustrated in FIG. 16C or 90° in an opposite direction relative to that illustrated in FIG. 16B. Nevertheless, image data can be acquired of the patient 14 during movement of the non-changing rotor portion 716 or at selected discrete positions as the rotor moves in the direction of arrows 734, 736. For example, an anterior-to-posterior and medial-to-lateral image can be acquired of the patient 14 to acquire two projections to the patient 14. Alternatively, or in addition thereto, a plurality of projections can be acquired through the patient 14 as the non-changing portion 716 moves relative to the patient 14.

In the "C"-shaped configuration, the imaging system 700 may acquire one or more two-dimensional (2D) images. The 2D images are acquired as image data that may be then transformed to three-dimensional (3D) images. The 2D or 3D images may be viewed by the user, such as a surgeon, for assisting in selected procedures. The images may be registered to a patient space, as is understood in the art, for performing a navigated surgical or other selected procedure. Further, the images may be used for determining or viewing selected portions of the patient anatomy.

In various embodiments, the imaging system, as discussed herein, may also be changed to an "O"-shaped configuration. In the "O"-shaped configuration the imaging system 700 may acquire images similar to those in other generally known CT-imaging systems. The images may be used to generated 3D images of the patient 14. Further, the "O"-shaped configuration may be used to acquired images at any selected perspective relative to the patient 14. Thus, the imaging system 700 may be provided to provide a changeable or alterable imaging system between a "C"-shaped imagine configuration to an "O"-shaped configuration.

Further, the imaging system 700, according to various embodiments including various embodiments as discussed above, may be provided as a compact imaging system. In particular, the imaging system 700 may be configured to the "C"-shaped configuration for mobility and storage purposes. In various embodiments, the rotor 710 may have a height 710$x$ at a selected highest or upper most point 710$y'$ of the rotors 710 above a floor or surface 710$y$ that supports the imaging system 700, similar in dimensions as discussed above. For example, the height may be about five feet. Thus, the imaging system need not be maintained in the "O"-shaped configuration at all times. This allows the imaging system 700 to acquire images in a CT-imaging system manner (e.g. with a full 360 degree spin around the patient 14) or in a C-arm configuration with the single imaging system 700.

While the rotor 710 may move, as discussed above, the source and detectors 36, 38, 40 can also be moved with appropriate movement mechanisms. For example, individual motors (36$a$, 38$a$, and 40$a$), such as servomotors, can be connected to the source 36 and the detectors 38, 40, respectively. Instructions may be sent to the servomotors 36$a$, 38$a$, and 40$a$ and to cause them to activate and move by instructions from the imaging computer 32 and/or based on input from a user. Also, the source 36 and the detectors 38, 40 can be moved by connections, such as belt connections with the motor 100. The movement of the source 36 and the detectors 38, 40 can be powered according to various systems, including those generally known in the art. The operation protocol for moving the source 36 and the detectors 38, 40 will be discussed in further detail herein.

In addition to and alternatively to moving the non-changing segment 716 as illustrated from FIGS. 16B to 16C or vice versa, as discussed above, the movable segment 750, as illustrated in FIG. 16D, can be moved from either end 718, 720 of the non-changing segment 716. As illustrated in FIG. 16D, the movable segment 750 can move to exit from the end 718 generally in the direction of arrow 752. The movable segment 750 can define an internal volume similar to an internal volume defined by the non-changing segment 716 to allow movement of the source 716 and the detectors 38, 40 therein.

The movable segment 750 extends from a first end 756 to a second end 758 generally along an arc length. The movable segment 750 can further include an exterior tooth portion 760 similar to the tooth portion 712 of the non-changing segment 716. The movable segment 750 can continue moving to any appropriate configuration relative to the non-changing segment 716 such as until a complete circle or total "O" configuration is achieved, such as an "O"-shape, as illustrated in FIG. 16E.

The movable portion 750 can be used to form the "O"-shaped configuration of the imaging system 700, including the rotor 710, as illustrated in FIG. 16E. As discussed above, the "O"-shaped configuration may allow the source 36 and the detectors 38, 40 to move generally in a 360° motion around the patient 14. When the rotor 710 is in the "O"-shape, the isocenter 110 may not change from when the rotor is in the "C"-shaped configuration. Thus, the isocenter 110 may be constant for the imaging system 700. The patient 14 may be positioned at or near the isocenter 110, including a selected portion of the patient of which image data is selected to be acquired.

The movable portion 750 can have a portion of the rail 730 formed therein such that when the movable segment 750 completes the "O"-shaped configuration, the source 36 and the detectors 38, 40 can traverse 360° around the isocenter 110 on the rail 730. Further, the tooth surface 760 can be moved into alignment with the tooth surface 712 so that the rotor 710 may also move relative to the patient 14. It is understood, however, that the rotor 710 need not move in a 360° movement as the source 36 and detectors 38, 40 can move 360° within the rotor 710 once the movable segment 750 is moved to connect the first end 718 and the second end 720 to allow movement of the source 36 and the detectors 38, 40 within the "O"-shape of the rotor 710, as illustrated in FIG. 16E.

Further, as discussed above, the rotor 710 can be moved relative to the cart 30 via the connection 147. For example, the connection 147 can be moved up and down generally in the direction of double-headed arrow 770 and back and forth as illustrated by a double-headed arrow 772. Further, the connection 147 can move the rotor 710 in a sway movement such as illustrated by the double-headed arrow 774 around an axis, such as an axis 776.

Therefore, the imaging system 700 can include the rotor 710 that can be change from a "C"-shape, as illustrated in FIGS. 16A-16C to an "O"-shaped configuration as illustrated in FIG. 16E. Further, the imaging system 700 can include the rotor 710 that achieves the configuration between the "C"-shape and the "O"-shape, as illustrated in FIG. 16D. It is further understood that the movable segments 750 can extend from either of the ends 718 or 720. Therefore, the movable segment 750 may extend from the end 720 and move towards the end 718 generally in the direction opposite of the arrow 752.

The changeability of the imaging system 700 from the "C"-shaped configuration to the "O"-shaped configuration also allows the single imaging system 700 (and according to various embodiments as discussed above) to operate in various manners without moving the patient 14. For example, the imaging system 700 may be operated as a "C"-arm to acquire selected 2D images while allowing great access to the patient 14. The imaging system 700 may also acquire CT type images using data acquired during a 360 spin around the patient. The different images may be acquired of the patient without moving the patient 14. This may allow the single imaging system 700 to operate in various manners during a single procedure, such as an operative procedure, without requiring movement of the patient 14 or altering a position of the patient 14 during the procedure.

The imaging system 700 including the source 36 and detectors 38, 40 can be operated according to various schemes to ensure or assist in ensuring that the source 36 is positioned opposite a selected one of the detectors 38, 40. As discussed above, the source 36 may move independently of the detectors 38, 40 relative to the rotor 710. Therefore, operation of the source 36 relative to the detectors 38, 40 may be necessary to ensure that the source 36 is opposite the detectors 38, 40 for imaging. Further, it is understood, that the imaging system 700 may include only a single one of the detectors 38, 40. For the following discussion the detector 38 would be specifically included for clarity. It is understood, however, that the control schemes discussed herein can be used to operate the imaging system 700 including a plurality of the detectors 38, 40.

Figure 17:
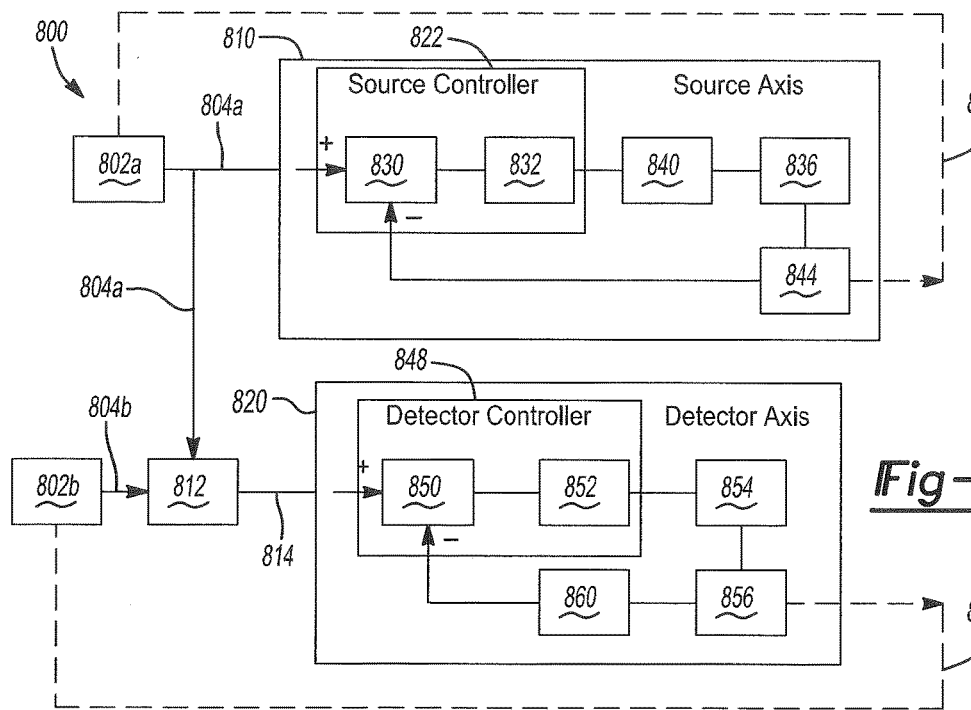
FIG. 17 is a flowchart illustrating a first control scheme.

With initial reference of FIG. 17 a command (referred to as a co-command) scheme is illustrated in a flowchart 800 where various portions referred to therein may include either or both hardware components specifically designed for the disclosed purpose, include firmware software for performing a disclosed purpose, or a general purpose processor that is executing software for a disclosed purpose. As discussed above, a user may operate the imaging system 700 from the cart 30 or other appropriate processor communicating and/or connected with the imaging system 700. For example, the user may operate the imaging system processor 32 via input, such as the pointer 702 (as illustrated in FIG. 16A) or a keyboard that is interconnected with the cart 30. The user can input a command that directs the imaging system processor 32 to operate and/or move various portions of the imaging system 700, including the source 36 and the detector 38. As illustrated in the flowchart 800, a command may be provided in a command block 802a and a command block 802b. The two command blocks 802a, 802b operate the control scheme in the flowchart 800 as a co-command control scheme. The command blocks 802a and 802b may include instructions based on the input by the user from the controller 32 and produce signals based thereon.

The command from the command block 802a may be sent as a signal 804a to a source axis 810. The command from the command block 802b may be the an offset signal from the signal 804a and can be sent as signal 804b. The offset signal 804b may be offset, as discussed further herein, from the signal 804a. The signal 804a may also be sent or diverted from the signal line 804a to a summing junction 812. The summing junction may both sum and subtract signals, as is generally known by one skilled in the arts. The offset signal 804b can be transmitted by the combiner block 812.

The offset can be any appropriate offset, such as about 150° to about 230°, including exactly 180°. As discussed above, the source 36 may generally be positioned substantially opposite or 180° from the detector 38 to acquire images of the patient 14. When the source 36 is substantially 180° from the detector 38, image data (and images based thereon) may be acquired as x-rays pass through the patient 14 on a substantially straight line from the source 36 to the detector 38. The signal from the command block 802b, therefore, can be provided 180° offset or separate from command block 802a and the signal 804a sent to the source axis 810 as the offset transmitted signal 814.

The offset signal 814 can then be sent to the detector axis 820. The source axis 810, as illustrated in the flowchart 800, can include both control mechanisms (e.g. PID controllers) and plant mechanisms (e.g. servomotor 36a) that are included with or within the source 36 to move the source 36. Further, the detector axis 820 can also refer to control mechanisms (e.g. PID controllers) and plant mechanisms (e.g. servomotor 36a) with or within the detector 38.

The signal 804a may reach the source axis 810 and be received by a source controller 822. The source controller 822 may include a controller summing junction 830 that initially receives the signal 804a and a controller 832. The summing junction may both sum and subtract signals, as is generally known in the controller arts. The controller 832 may be any appropriate controller (such as a proportional integral derivative controller (PID)). The controller 832 may transmit the signal 804a from the command input 802a and to a plant mechanism 836 through, optionally, an amplifier 840. The plant mechanism 836 may include the servomotor 36a that is used to move or drive the source 36 to a selected position. The signal 804a from the command module 802a can be provided to the plant mechanism 836 to move or power the servomotor 36a, acting as the plant mechanism 836, to position the source 36 at a selected location.

A signal from the plant mechanism 836 can then be transmitted to an encoder 844 to sense a position of the source 36. A signal of the sensed position from the encoder 844 can be provided back to the summing junction 830 to assist in controlling the position of the source 36 and/or a speed of travel of the source 36. The encoder 844 may, however, generate a signal separate from the plant mechanism 836 to determine an absolute position, relative position, or amount of movement of the source 36 over a period (e.g. since last movement or since start of movement). Therefore, the source 36 can be moved in a first direction based upon the signal 804a from the command module 802a.

The detector axis 820 can include components similar to the source axis 810, including a detector controller 848. The detector controller 848 may include a detector summing junction 850 that receives the offset signal 814 from the combiner 812. The offset signal, being offset by 180°, can operate to move the detector to a position or in a direction opposite the movement of the source 36. Further, as the offset signal is 180° of that of the source 36, the detector 38 may generally be moved substantially opposite the source on the rotor 710.

Accordingly, the signal can pass from the summing junction 850 to a detector controller 852 (which may be any appropriate controller, such as a PID controller) and then be provided, optionally, through an amplifier 854 to a plant mechanism 856. As discussed above, the plant mechanism 856 may be the servomotor 38a, as discussed above, provided with the detector 38. Therefore, the offset signal 814 can be used to operate the plant mechanism 854 to move the detector 38 substantially opposite the source 36.

The detector axis 820 may further include a detector encoder 860, similar to the source encoder 844. A signal from the plant mechanism 856 can then be transmitted to the detector encoder 860 to sense a position of the detector 38. A signal of the sensed position from the detector encoder 860 can be provided back to the summing junction 850 to assist in controlling the position of the detector 38 and/or a speed of travel of the detector 38. The detector encoder 860 may, however, generate a signal separate from the plant mechanism 856 to determine an absolute position, relative position, or amount of movement of the source 36 over a period (e.g. since last movement or since start of movement).

Further, output signals from the source axis 810 can include an output signal 870 to the command module 802a. In a similar manner, an output signal 872 from the detector axis 820 can be provided to the command module 802b. The signals provided to the command modules 802a, 802b can be used to confirm positioning of the source 36 and the detector 38 at the selected positions in the rotor 710.

Accordingly, the control mechanism or scheme 800, illustrates how the source axis 810 (which includes the source 36) and the detector axis 820 (which includes the detector 38) receive selected signals and use the signals to control movement of the respective source 36 and detector 38. The control scheme 800, therefore, illustrates how the source 36 can be moved substantially to a position opposite of the detector 38. In this manner, the source 36 can be moved to any selected relative to the patient on the rotor 710, but also be substantially opposite the detector 38 based upon an input from the user.

Figure 18:
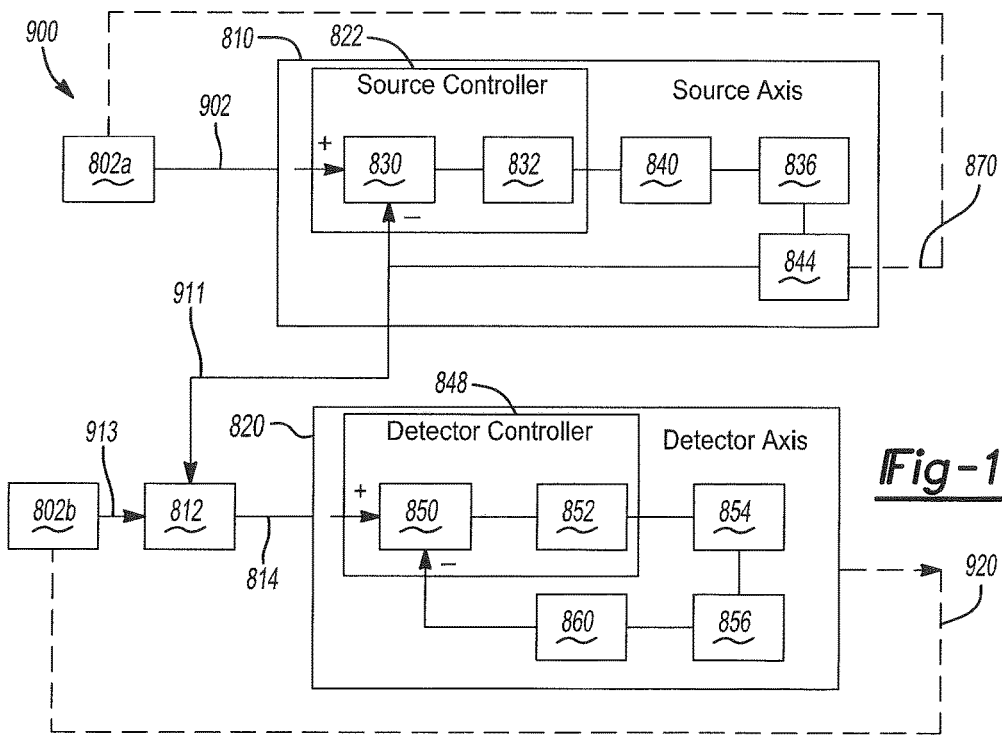
FIG. 18 is a flowchart illustrating a second control scheme.

The flowchart 800 illustrates at least one control or co-command scheme for controlling the movements of the source 36 relative to and with movement of the detector 38. According to various embodiments, FIG. 18 illustrates an alternative or second control scheme as a master-slave scheme illustrated in the flowchart 900. In the master/slave control scheme, various components and controllers may be substantially similar as in the co-command scheme according to the flowchart 800, but may be operated in a different manner, as discussed herein. As discussed above in relation to the co-command scheme 800, the command modules 802a, 802b may provide signals, as discussed herein, to the source axis 810 and the detector axis 820. As discussed above, the respective axes 810, 820 may include controllers and plant mechanisms to control and move the respective source 36 and detector 38.

A signal 902 is sent from the command block 802 to the source axis 810. The source axis 810 can include the same components as illustrated in the command scheme 800 and will not be described in detail, but mentioned briefly. Initially, the signal can be received within the source controller 822 including the summing junction 830 and then transmitted to the controller 832 (which may be a PID controller as discussed above). The signal may then be, optionally, amplified in the amplifier 840 and used to drive the plant or power mechanism 836. An encoder may receive a signal form the plant 836 and/or sense a position of the source 36 and return a signal to the summing junction 830 in the source controller 822.

The master/slave control scheme 900 may differ from the co-command control scheme 800 in that the detector axis 820 may receive a signal from the source axis 810, including a signal 911 from the encoder 844, rather than responding directly to a signal 913 from the command module 802b. The signal 913 from the command module 802b may include an offset, such as the offset discussed above. As discussed above, the offset may be about 150° to about 230°, including exactly 180°, to produce the offset signal 814.

The signal 911 from the source axis 810 may go to the summing junction 812 that also receives the signal 913 from the command module 802b. From the summing junction 812 the offset signal 814 may then be transmitted to the detector axis 820. Thus, the detector axis 820 receives the signal 911 from the source axis 820 prior to any action, therefore the detector axis is a slave to the source axis 810. It is understood, however, that the source axis 810o may be a slave to the detector axis 820.

The offset signal 814 is initially received within the detector controller 848 including the summing junction 850 and transmitted to the controller 852 (which may be a PID controller, as discussed above). The signal may then be, optionally, amplified in the amplifier 854 and transmitted to the plant/motor 856. An encoder 860 may also be used to determine a position signal of the detector 38, as discussed above. An output signal 920, optionally, can then be provided to the command module 802b to determine whether the final position based upon input of the use of the source 36 and the detector 38 has been reached.

In the master/slave command scheme 900, the signal to the detector axis 820 is based, at least in part, upon the output signal 911 from the source axis 810. Therefore, the detector 38 only moves based upon movement, as encoded in the signal 911, output from the source axis 810. This can allow the slower component, for example the source 36, to dictate movement of the faster moving component, for example the detector 38. This may ensure that the two components can reach a selected position at a selected time in synchronization. It is understood, however, that the source may not be the faster moving component; this is simply provided for the current discussion.

Further, it is understood that the offset signal 814 may not be a 180° offset. For example, the signal 902 may be a −90° signal and the offset signal and the offset signal 814 may be a +90° signal. As the detector 38 moves based upon an output signal from the source axis 810, the detector 38 would still be 180° separated from the source 36.

Figure 19:
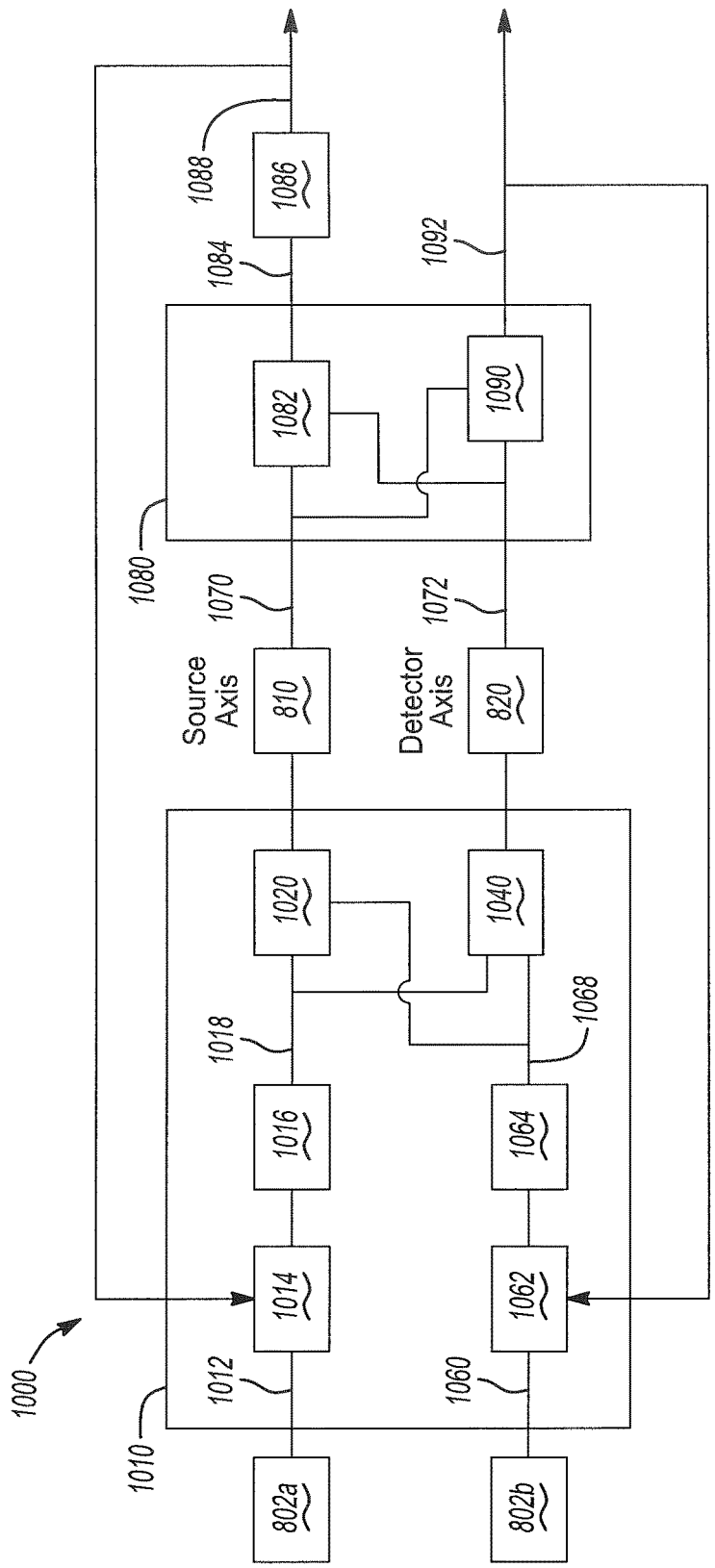
FIG. 19 is a flowchart illustrating a third control scheme.

An average and difference command scheme 1000 is illustrated in FIG. 19. The command scheme 1000 is a further alternative to controlling movement of the source 36 and the detector 38 relative to one another within the imaging system 700. The control scheme 1000 may include various components similar to that discussed above, that are not discussed in further detail here, but only briefly listed here. The control scheme 1000, nevertheless, may include a first control module 1010 that may be includes or provided in the imaging processor 32 or other appropriate processor. The first control module 1010 can include various components as discussed herein, which may be embodied in the processor 32 or other appropriate processor. The first control module 1010 may include firmware included with a processor or include programmable software that is executed by a general processor. Further, the first control module 1010 may be a separate component that is interconnected with the imager 700 that may receive an input from the user for positioning the source 36 and the detector 38. The input from the user may be provided with or from the command modules 802a, 802b, as discussed above.

The first control module 1010 in controlling the position of the source 36 and the detector 38 can receive an input from the user regarding a selected position from the command modules 802a, 802b. The first control module 1010 can receive an input regarding an average speed of the system as input 1012 which goes to an initial summing junction 1014 then to a first controller 1016 (such as a PID controller). An output signal from the controller 1016 may be an output signal 1018 that is transmitted to a second summing junction 1020 and to the source axis 810. The source axis 810 may include various components, including those components discussed above in the source axis 810. The various components will not be further discussed here, however, the source axis 810 may include the controller and the plant mechanism for moving the source 36 and the encoder or a sensor for sensing movement of the source 36.

The signal 1018 may further be transmitted to a third summing junction 1040 and transmitted to the detector axis 820. Again, the detector axis 820 can include components as discussed above in the detector axis 820, and are not reiterated here. For example, the detector axis 820 may include the controller, to the plant mechanism to move the detector 38, and the encoder to determine or sense a position of the detector 38.

The first control module 1010 can further receive a difference signal 1060 from the command module 802b that may include the offset of the detector 38 relative to the source 36. The difference signal 1060 may be transmitted to a fourth summing junction 1062 and to a second controller 1064 (which may be a PID controller). An output signal 1068 from the controller 1064 may be transmitted to the third summing junction 1040 and to the second summing junction 1020. The signal from the two summing junctions 1040, 1020 can then be provided, respectively, to the detector axis 820 and the source axis 810. Therefore, each of the detector axis 820 and the source axis 810 may receive signals regarding both the average speed and difference in speed of the two axes 810, 820.

The source axis 810 can then output a source axis signal 1070 and the detector axis 820 can output a detector axis signal 1072 to a signal conditioning module 1080. The signal conditioning module 1080 may also include firmware executed by a selected processor or programmable software executed by a selected processor. In the signal conditioning module 1080, a summation of the source axis output signal 1070 and the detector axis output signal 1072 may be made in a fifth summing junction 1082 and a summation signal 1084 is then divided in half in a computation or average module 1086 and an average signal 1088 may be output from the computation module 1086. The signal conditioning module 1080 further includes a summing junction 1090 which may output a difference signal 1092 as a difference between the source axis output signal 1070 and the detector axis output signal 1072. Both the averaging signal 1088 and the difference signal 1092 can be input to the first control module 1010 to control the position of the detector 38 and the source 36 to provide feedback regarding an instant position and/or speed of the source 36 and detector 38.

As discussed above, the imaging system 700 includes the source 36 and the detector 38 (and/or the detector 40) that may move relative to one another within the rotor 710. As the source 36 and the detector 38 may move relative to one another, various control schemes, including those discussed above and illustrated in the control schemes 800, 900, and 1000, may be used to control position of the source 36 and the detector 38 relative to one another. The control scheme allows the source 36 and the detector 38 to be selectively movable relative to one another without being positioned on a rigid connection system. As the source 36 and the detector 38 are able to move relative to one another, selected perspectives of the patient 14 may be acquired which may vary beyond those allowed if the source 36 and the detector 38 are rigidly positioned relative to one another on a fixed mechanism, such as an arcuate structure. Therefore, the control schemes allow the control of the position of the source 36 relative to the detector 38 for imaging of the patient 14. Further, the control schemes can ensure that at selected times the source 36 is substantially opposed to the detector 38 for acquiring images of the subject 14. It is further understood, however, that a non-human patient may be imaged with the imaging system 700.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. An imaging system configured to acquire images of a subject, comprising:
   a source configured to emit an energy;
   a detector configured to detect the emitted energy and generate image data based on the detected emitted energy;
   a base; and
   a track attached to the base and extending along an arc around a center;
   wherein both the source and the detector are individually and independently moveable on the track along the arc around the center from a first position to a second position, wherein the second position has a greater distance between the source and the detector than the first position;
   wherein both the source and the detector are configured to move along the arc around the center independently on the track.

2. The imaging system of claim 1, wherein the track includes a first segment and a second segment;
   wherein the second segment is moveable relative to the first segment to change a shape of the track from a first configuration to a second configuration.

3. The imaging system of claim 2, wherein the second segment is configured to move relative to the first segment to form a complete 360 degree annular track;
   wherein both the source and the detector are configured to move 360° on the annular track.

4. The imaging system of claim 1, wherein the detector includes a first detector and a second detector.

5. The imaging system of claim 4, wherein the first detector is configured to move independent of the second detector.

6. The imaging system of claim 1, further comprising:
   a gantry;
   wherein the gantry is fixed relative to the base and the track is configured to move relative to the gantry.

7. The imaging system of claim 1, wherein at least a portion of the track is fixed relative to the base.

8. The imaging system of claim 1, wherein the track is movable relative to the base.

9. The imaging system of claim 8, wherein the track has a fixed length between a first end and a second end of the track.

10. The imaging system of claim 1, wherein the track is positioned within a rotor that houses the source and the detector;
    wherein when the source is on the track, the source is a first distance to the center;
    wherein when the detector is on the track, the detector is a second distance to the center;
    wherein the first distance is the same as the second distance.

11. The imaging system of claim 10, further comprising:
    a gantry;
    wherein a length of the rotor is greater than a length of the gantry.

12. The imaging system of claim 1, wherein the base is a mobile base configured to move the imaging system from a first location to a second location.

13. An imaging system configured to acquire images of a subject, comprising:
    a source configured to emit an energy;
    a first detector configured to detect the emitted energy and generate first image data based on the detected emitted energy;
    a second detector configured to detect the emitted energy and generate second image data based on the detected emitted energy;
    a mobile cart; and
    a track extending from a first end to a second end and attached to the mobile cart and extending along an arc around a center;
    wherein each of the source, the first detector, and the second detector are individually and independently movable between the first end to the second end on the track along the arc and around the center.

14. The imaging system of claim 13, wherein the track includes a first arcuate segment and a second arcuate segment;
    wherein the second arcuate segment is movable relative to the first arcuate segment to change a shape of the track from a first configuration to a second configuration.

15. The imaging system of claim 14, wherein the second arcuate segment is configured to move relative to the first arcuate segment to form an O-shaped track;
    wherein each of the source, the first detector, and the second detector are configured to move 360° on the O-shaped track along the arc and around the center.

16. The imaging system of claim 13, wherein at least a portion of the track is fixed relative to the cart.

17. The imaging system of claim 13, wherein the track is movable relative to the cart.

18. The imaging system of claim 13, further comprising:
    a gantry; and
    a rotor;
    wherein a length of the rotor is greater than a length of the gantry;
    wherein the track is positioned within the rotor that houses the source and the detector.

19. An imaging system configured to acquire images of a subject, comprising:
    a mobile cart;
    a rotor having a track that extends along an arc and around a center from a first end to a second end, the rotor attached to the mobile cart;

a source configured to emit an energy; and a detector configured to detect the emitted energy and generate image data based on the detected emitted energy;

wherein both the source and the detector are individually and independently movable on the track along the arc and around the center between the first end and the second end from a first position to a second position, wherein the second position has a greater distance between the source and the detector than the first position.

20. The imaging system of claim 19, wherein the rotor is movable relative to the mobile cart.

21. The imaging system of claim 19, wherein the rotor is fixed relative to the mobile cart.

* * * * *